(12) United States Patent
Shepherd et al.

(10) Patent No.: US 10,966,694 B2
(45) Date of Patent: Apr. 6, 2021

(54) APPARATUS AND METHOD FOR MEDICAL IMAGING AND PATHOLOGY CORRELATIONS

(71) Applicant: NEW YORK UNIVERSITY, New York, NY (US)

(72) Inventors: Timothy Shepherd, Tarrytown, NY (US); Ryan Brown, New York, NY (US); Mary Bruno, New York, NY (US)

(73) Assignee: NEW YORK UNIVERSITY, New York, NY (US)

(*) Notice: Subject to any disclaimer, the term of this patent is extended or adjusted under 35 U.S.C. 154(b) by 184 days.

(21) Appl. No.: 16/022,103

(22) Filed: Jun. 28, 2018

(65) Prior Publication Data

US 2019/0000431 A1    Jan. 3, 2019

Related U.S. Application Data

(60) Provisional application No. 62/526,945, filed on Jun. 29, 2017.

(51) Int. Cl.
*A61B 16/00* (2006.01)
*G01N 1/06* (2006.01)
(Continued)

(52) U.S. Cl.
CPC .......... *A61B 16/00* (2013.01); *G01N 1/06* (2013.01); *G01N 1/286* (2013.01);
(Continued)

(58) Field of Classification Search
CPC .......... A61B 16/00; G01N 1/06; G01N 1/286; G01R 33/30; G01T 7/02
See application file for complete search history.

(56) References Cited

U.S. PATENT DOCUMENTS

| | | | | |
|---|---|---|---|---|
| 1,892,861 A | * | 1/1933 | Welty | ............ A01J 23/00 249/53 R |
| 2,104,278 A | * | 1/1938 | Schultz | ............ B26B 29/063 83/761 |

(Continued)

OTHER PUBLICATIONS

D'Arceuil, H.E., et al., "An approach to high resolution diffusion tensor imaging in fixed primate brain", Neuroimage, 2007, 35:553-565.

(Continued)

*Primary Examiner* — Brian J. Sines
(74) *Attorney, Agent, or Firm* — Foley & Lardner LLP

(57) ABSTRACT

A primary sample holder for imaging, gross pathology, or histological correlations of a biological sample includes an enclosure having a first side wall, a second side wall, and a bottom wall; a plurality of slots provided at predetermined intervals along the first and second side walls; and a grid recessed within the bottom wall. The grid includes a hole bisected by a central panel and at least one axial panel that intersects the central panel along a length thereof. The biological sample received by the primary sample holder is configured to be aligned with the central panel of the grid to align the biological sample along an accepted internal orientation line (e.g., the anterior-posterior commissure line in the brain). The slots are configured to receive a cutting device to cut the biological sample into slices of uniform thickness containing a region of interest based on histological and imaging findings.

14 Claims, 21 Drawing Sheets

(51) Int. Cl.
*G01R 33/30* (2006.01)
*G01T 7/02* (2006.01)
*G01N 1/28* (2006.01)
*G01N 33/483* (2006.01)
*G01N 1/00* (2006.01)

(52) U.S. Cl.
CPC ......... *G01N 33/4833* (2013.01); *G01R 33/30* (2013.01); *G01T 7/02* (2013.01); *G01N 2001/002* (2013.01); *G01N 2001/2873* (2013.01)

(56) References Cited

U.S. PATENT DOCUMENTS

| | | | | |
|---|---|---|---|---|
| 3,058,503 | A | * | 10/1962 | Perakis ................ B26B 29/063 83/764 |
| 3,816,919 | A | * | 6/1974 | Portnoy ................ A61B 17/32 30/124 |
| 3,965,573 | A | * | 6/1976 | Mims .................... A61B 16/00 30/124 |
| 3,987,541 | A | * | 10/1976 | Sieczkiewicz ......... A21C 15/04 30/114 |
| 5,136,906 | A | * | 8/1992 | Antonissen ........ A22C 17/0033 382/110 |
| 5,612,819 | A | * | 3/1997 | Meyer .................... G02B 21/34 356/244 |
| 5,831,763 | A | * | 11/1998 | Meyer .................... G02B 21/34 359/391 |
| 2017/0199104 | A1 | * | 7/2017 | Gradinaru ............ C12Q 1/6841 |

OTHER PUBLICATIONS

Ding, S-L., et al., "Comprehensive Cellular-Resolution Atlas of the Adult Human Brain", J Comp Neurol, 2016, 524:3127-3481.

Goubran, M., et al., "Image registration of ex-vivo MRI to sparsely sectioned histology of hippocampal and neocortical temporal lobe specimens", Neuroimage, 2013, 83:770-781.

Goubran, M., et al., "Registration of in-vivo to ex-vivo MRI of surgically-resected specimens: A pipeline for histology to in-vivo registration", J Neurosci Methods, 2015, 241:53-65.

Miller, K.L., et al., Diffusion imaging of whole, post-mortem human brains on a clinical MRI scanner, Neuroimage, 2011, 57:167-181.

Nir, G., "Model-Based Registration of Ex Vivo and In Vivo MRI of the Prostate Using Elastography", IEE Trans Med Imaging, Jul. 2013, 32(7):1349-1361.

Pfefferbaum, A., et al., "Postmortem MR imaging of formalin-fixed human brain", Neuroimage, 2004, 21(4):1585-1595.

Shatil, A.S., et al., A Method for Whole Brain Ex Vivo Magnetic Resonance Imaging with Minimal Susceptibility Artifacts, Front Neurol, Nov. 29, 2016, vol. 7, Article 208, pp. 1-10.

Trivedi, H., et al., "Use of Patient-specific MRI-based Prostate Mold for Validation of Multiparametric MRI in Localization of Prostate Cancer", Urology, 2012, 79:233-239.

Absinta, M., et al., "Postmortem Magnetic Resonance Imaging to Guide the Pathologic Cut: Individualized, 3-Dimensionally Printed Cutting Boxes for Fixed Brains", J Neuropathol Exp Neurol., Aug. 2014, 73(8):780-788.

* cited by examiner

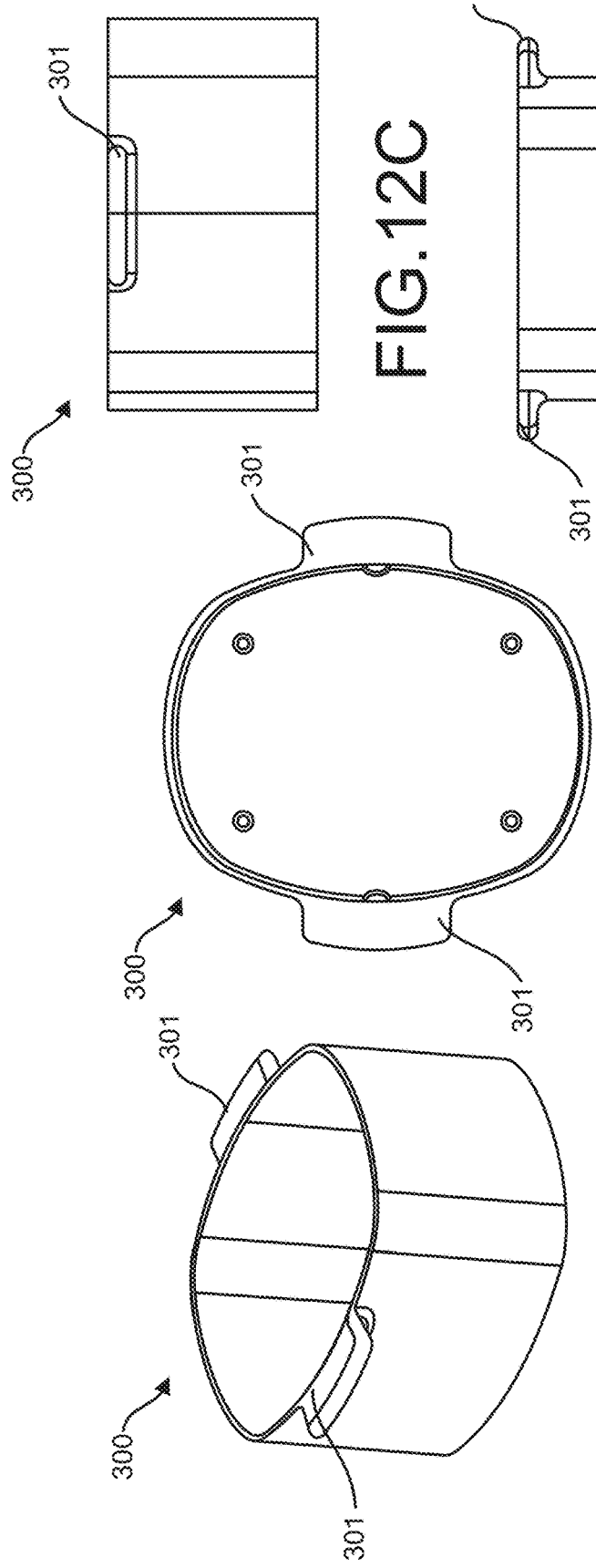

Securing attachment

APPARATUS AND METHOD FOR MEDICAL IMAGING AND PATHOLOGY CORRELATIONS

CROSS-REFERENCE TO RELATED APPLICATIONS

This application claims priority to U.S. Provisional Application No. 62/526,945, filed Jun. 29, 2017, which is incorporated herein by reference in its entirety for all purposes.

STATEMENT OF GOVERNMENT INTEREST

This invention was made with government support under contract no. NIA 1K23AG048622-01 awarded by the National Institutes of Health. The government has certain rights in the invention.

FIELD OF THE INVENTION

The present invention relates generally to the field of medical imaging and pathology. More specifically, the present invention relates to an apparatus and method of identifying a precise location, orientation, and thickness of cuts to be made to a biological sample for subsequent imaging, gross pathology, or determination of histological correlations of the biological sample.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

There has been a recent interest in the radiology, pathology, neurology, neurosurgery and research community to image ex vivo organs such as brains with CT, MRI or other imaging techniques. From a forensic pathology perspective, this can help identify pathological abnormalities in the organ that may not be detected during a gross pathologic examination of the organ after it is fixed in formaldehyde before or even after the tissue or organ cut into coronal, axial, sagittal or specific oblique slices. Imaging ex vivo organs also can increase the yield of positive cases in which cutting and histopathology of organs that have a normal MRI appearance are deferred to save time and money expended towards the autopsy. Conventionally, gross specimens are sampled from the organ in a consistent manner depending on the a priori assumption of the underlying abnormality. For example, when the organ is a brain, the entorhinal cortex, hippocampal body, posterior cingulate gyms, etc. may be sampled for Braak staging in Alzheimer's disease pathology (i.e., portions of the brain known to be associated with Alzheimer's disease are sampled). In this example, unexpected areas of neuropathology outside the consistently sampled regions would only be recognized if the neuropathologist visually appreciated the abnormality on gross inspection and sampled the unexpected location for histology analysis—imaging the sample before selecting samples can therefore improve diagnostic yield. Known radiology-pathology correlations also can be used to validate and develop new imaging biomarkers of disease for living subjects. For example, a known radiology-pathology correlation is that T2 decreases with increasing beta-amyloid plaque deposition in cortical regions affected by Alzheimer's disease.

There are several limitations thus far for these clinical, translational and research studies. Referring to the example in which the organ is a brain, routinely the whole brain or a half brain (a single cerebral hemisphere) is cut manually without consistent orientation to the cardinal orientations used in the in vivo imaging of subjects or anatomic atlases (e.g. parallel or orthogonal to the plane formed between the anterior and posterior commissure). Further the ability to co-localize a histopathologic abnormality to the corresponding MRI images or CT images is not trivial and requires time-intensive post-processing of histology and MRI or CT images to link the images correctly. Further, this might only work for certain aspects of the cut brain and not the entire sample.

Currently, no standard technology exists for obtaining slices of a biological human tissue sample having uniform thickness across slices and within individual slices. Individual cutting templates for specific individual organs or tissues from a specific individual patient or subject have been described, but there is no technology that can be applied to all such samples without a priori information. In addition, no standard technology exists for obtaining accurate stereotactic co-localization of gross, histological and imaging findings for radiology-pathology correlations and research.

SUMMARY

In some embodiments, a system for imaging, gross pathology, or histological correlations of a biological sample includes a primary sample holder configured to receive the biological sample. The primary sample holder comprises an enclosure having a first side wall, a second side wall, and a bottom wall connected to the first side wall and the second side wall; and a plurality of slots provided at predetermined intervals along the first and second side walls. Each of the slots extends from a top of a respective one of the first side wall or the second side wall to a bottom of the respective one of the first side wall or the second side wall. The plurality of slots are configured to receive a cutting device configured to cut the biological sample into slices containing a region of interest based on gross visual and imaging findings.

In some aspects, the primary sample holder further comprises: a grid recessed within the bottom wall, the grid comprising a hole bisected by a central panel that runs along a longitudinal axis of the primary sample holder and at least one axial panel that intersects the central panel along a length thereof. The biological sample received by the primary sample holder is configured to be aligned with the central panel of the grid to align the biological sample along an accepted internal orientation line for imaging, cutting multiple individual biological samples in a same manner, and/or stereotaxis.

In some aspects, a top surface of the central panel and a top surface of the at least one axial panel is flush with a top surface of the bottom wall.

In some aspects, the system further includes a secondary sample holder configured to receive at least one slice of the biological sample produced in the primary sample holder. The secondary sample holder comprises a second enclosure having a front wall, a back wall, a first side wall, a second side wall, and a bottom wall; and a plurality of slots provided at predetermined intervals along the front wall, the back wall, the first side wall and the second side wall of the second enclosure. Each of the slots extends from a top of a respective one of the front wall, the back wall, the first side wall and the second side wall of the second enclosure to a bottom of the respective one of the front wall, the back wall, the first side wall and the second side wall of the second enclosure. The plurality of slots provided in the front wall, the back wall, the first side wall and the second side wall of the second enclosure are configured to receive the cutting device to cut the at least one slice of the biological sample produced in the primary sample holder in one or two additional planes.

In some aspects, the secondary sample holder further comprises a plurality of linear indentations formed in the bottom wall of the second enclosure. The plurality of linear indentations form a second grid configured to assist in reproduction of an orientation of the at least one slice produced in the primary sample holder.

In some aspects, the system further includes an outer shell configured to receive and hold either the primary sample holder or the secondary sample holder during an imaging process.

In some aspects, the primary sample holder further comprises a grid recessed within the bottom wall, the grid comprising a hole bisected by a central panel that runs along a longitudinal axis of the primary sample holder and at least one axial panel that intersects the central panel along a length thereof; the outer shell comprises an inner component and an outer component; the primary sample holder is configured to be inverted and received within at least one well formed in the inner component of the outer shell to secure the biological sample between the bottom wall of the primary sample holder and the inner component of the outer shell; and the biological sample is configured to be aligned with the central panel of the grid to align the biological sample along an accepted internal orientation line for imaging.

In some aspects, the primary sample holder and the biological sample therein are configured to be submerged in a fluid contained in the inner component of the outer shell during imaging.

In some aspects, the system further includes a secondary outer shell configured to receive and hold the outer shell during the imaging process. A space between the secondary outer shell and the outer shell contains air and/or a susceptibility-matching fluid, material, or ceramic configured to improve a signal-to-noise ratio for the biological sample in the primary sample holder In some aspects, the system further includes at least one securing attachment configured to hold the biological sample against the bottom wall of the primary sample holder such that the biological sample does not move during transportation into/out of an imaging device, between imaging and histology, or during an imaging or cutting process.

In some aspects, the system further includes an imaging device configured to image the biological sample using CT, MM or other imaging techniques.

In some embodiments, a method for imaging, performing gross pathology, or determining histological correlations of a biological sample includes placing the biological sample within a primary sample holder comprising an enclosure having a first side wall, a second side wall, and a bottom wall; a plurality of slots provided at predetermined intervals along the first and second side walls, each of the slots extending from a top of the first side wall or the second side wall to a bottom of the first side wall or the second side wall; and a grid recessed within the bottom wall, the grid comprising a hole bisected by a central panel that runs along a longitudinal axis of the primary sample holder and at least one axial panel that intersects the central panel along a length thereof. The method further includes aligning the biological sample with the central panel of the grid to align the biological sample along an accepted internal orientation line for imaging; and imaging the biological sample contained in the primary sample holder in an imaging device.

In some aspects, the method further includes placing the primary sample holder containing the biological sample within an outer shell prior to imaging the biological sample contained in the primary sample holder in the imaging device.

In some aspects, placing the primary sample holder within the outer shell comprises: inverting the primary sample holder; receiving the inverted primary sample holder within at least one well formed in the outer shell to secure the biological sample between the bottom wall of the primary sample holder and the outer shell; and aligning the biological sample with the central panel of the grid along an accepted internal orientation line for imaging.

In some aspects, the method further includes removing the primary sample holder from the imaging device and the outer shell; and cutting, based on images acquired by the imaging device, the biological sample into slices containing a region of interest. The imaging and cutting steps are performed while the biological sample remains in the primary sample holder in a same position to provide accurate stereotactic co-localization of gross, histological and imaging findings.

In some aspects, the method further includes placing a slice of the biological sample obtained in the cutting step into a secondary sample holder comprising a second enclosure having a front wall, a back wall, a first side wall, a second side wall, and a bottom wall; a plurality of slots provided at predetermined intervals along the front wall, the back wall, the first side wall and the second side wall of the second enclosure, each of the slots extending from a top of a respective one of the front wall, the back wall, the first side wall and the second side wall of the second enclosure; and a plurality of linear indentations formed in the bottom wall of the second enclosure, the plurality of linear indentations forming a second grid configured to assist in reproduction of an orientation of the slice. The method further includes performing a second cutting step to further cut the slice in one or two additional planes.

In some aspects, the method further includes imaging the slice contained in the secondary sample holder in the imaging device.

In some aspects, the method further includes placing the secondary sample holder containing the slice within the outer shell prior to imaging the slice contained in the secondary sample holder in the imaging device.

Any of the embodiments or aspects described above may be combined.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which:

FIG. 12A illustrates another embodiment of an outer shell from a perspective view. The outer shell may be used to contain a liquid in which the biological sample and inner primary sample holder are immersed. In this example, the outer shell has incorporated handles to facilitate transportation.

FIG. 12B illustrates the outer shell of FIG. 12A from a top view. The peg-like features are an example of how the inner primary sample holder may be elevated above the bottom surface of the outer shell to allow the free flow of liquid. Small grooves (e.g., two small grooves) on the sides may be used to fit the inner primary sample holder and restrict its motion within the outer shell.

FIG. 12C illustrates the outer shell of FIG. 12A from a side view.

FIG. 12D illustrates the outer shell of FIG. 12A from a front view.

DETAILED DESCRIPTION

Figure 1A:
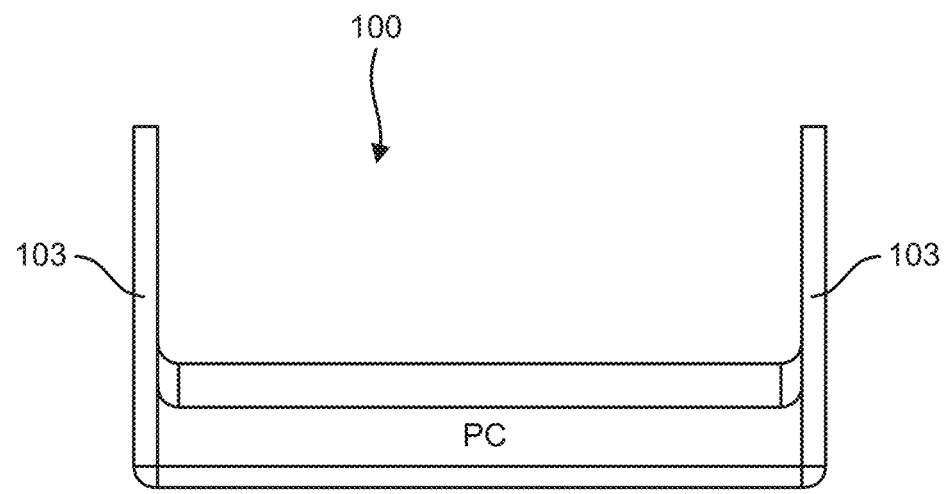
FIG. 1A illustrates a front view of a primary sample holder for imaging, transporting and cutting a biological sample without movement and with consistent, exact stereotactic coordinates.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

In general, the apparatus and method described below solves two existing problems not addressed by current technology. First, brain cutting for neuropathology is haphazard with typical postmortem cutting resulting in brain slices of varying thickness both across slices and within individual slices. This can lead to asymmetries during visual inspection of the gross brain slices, but also asymmetric sampling of paired structures (like the hippocampi). The apparatus and method described below will allow a user, including, but not limited to, medical examiners, forensic or clinical pathologists, to obtain slices of regularly-spaced and uniform cuts (e.g., uniform thickness of the slices) of a biological sample such as the whole brain or hemisphere in the desired plane relative to any desired coordinate system (axial, coronal, sagittal or oblique). Second, the apparatus and method will facilitate highly accurate stereotactic co-localization of gross, histological and imaging findings for radiology-pathology correlations, various clinical determinations and research. This is especially useful to clinical pathologists and medical examiners that perform standard autopsies and enhanced autopsy studies that incorporate radiology-pathology correlations.

Referring to FIGS. 1A-9C, an apparatus for correlating medical imaging and pathological analyses includes a primary sample holder 100, a secondary sample holder 200, and an outer shell 300. A biological sample 400 is configured to be placed within either the primary sample holder 100 or the secondary sample holder 200. In the examples of FIGS. 1A-9C, the biological sample 400 is a whole brain or a hemisphere of a brain, but the applications of the apparatus are not limited in this regard. Other biological samples 400, for example, other organs such as the heart, kidney, or liver; specific parts of an organ such as a cerebral hemisphere or a temporal lobe of the brain; muscles; or tissue samples, may be examined using the apparatus. The biological sample 400 remains in the primary sample holder 100 or the secondary sample holder 200, in the same position, for both the medical imaging and pathological analysis processes. The primary sample holder 100, the secondary sample holder 200, and the outer shell 300 are made from materials that are compatible with medical imaging techniques such as magnetic resonance imaging (MRI), computerized tomography (CT or CAT) scans, radiographs, ultrasound imaging, or positron emission tomography (PET) scans to allow the apparatus to be used in both the medical imaging and pathological analyses, using the same orientations. As a result, the facility of performing radiology-pathology correlations using exact stereotactic coordinates is greatly increased. MM compatible versions of the apparatus can be specifically designed for any MRI field strength (e.g., 1.5-T, 3-T, 7-T, 9.4-T or 11-T, which are commonly used clinically and in translational/basic research).

One or more of the primary sample holder 100, the secondary sample holder 200, and the outer shell 300 may be manufactured with 3D printing. As will be discussed in further detail below, the primary sample holder 100 and the secondary sample holder 200 can be used to hold a biological sample (e.g., an organ) of any size or shape. The primary sample holder 100 is configured to receive and hold therein a biological sample 400 for imaging, transporting, and/or cutting the biological sample 400 (e.g., cutting the biological sample 400 into slices). The secondary sample holder 200 is configured to receive and hold therein a slice of the biological sample 400 that was cut when the biological sample 400 was held in the primary sample holder 100. The slice of the biological sample 400 may be further imaged, transported, and/or cut while held in the secondary sample holder 200. The outer shell 300 is configured to receive and hold therein the primary sample holder 100 or the secondary sample holder 200 during imaging.

Primary Sample Holder

Figure 1B:
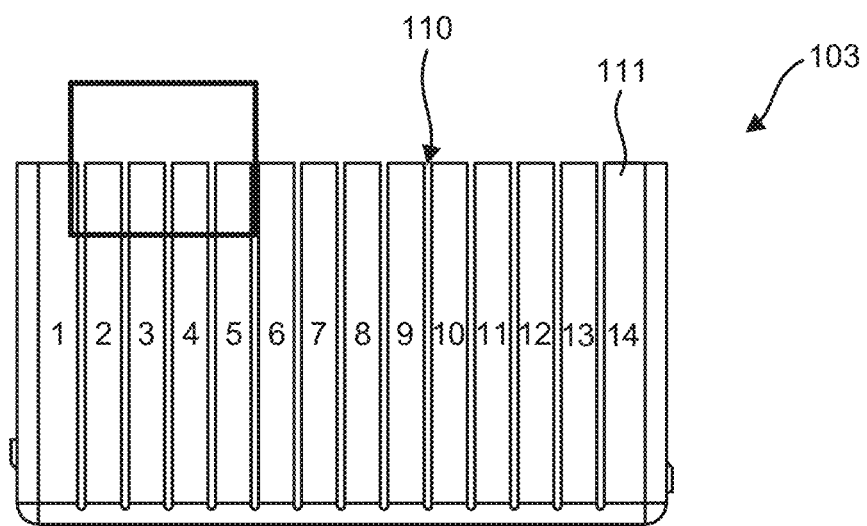
FIG. 1B illustrates a side view of the primary sample holder of FIG. 1A, which includes slots or gaps configured to receive a cutting device.
Figure 1C:
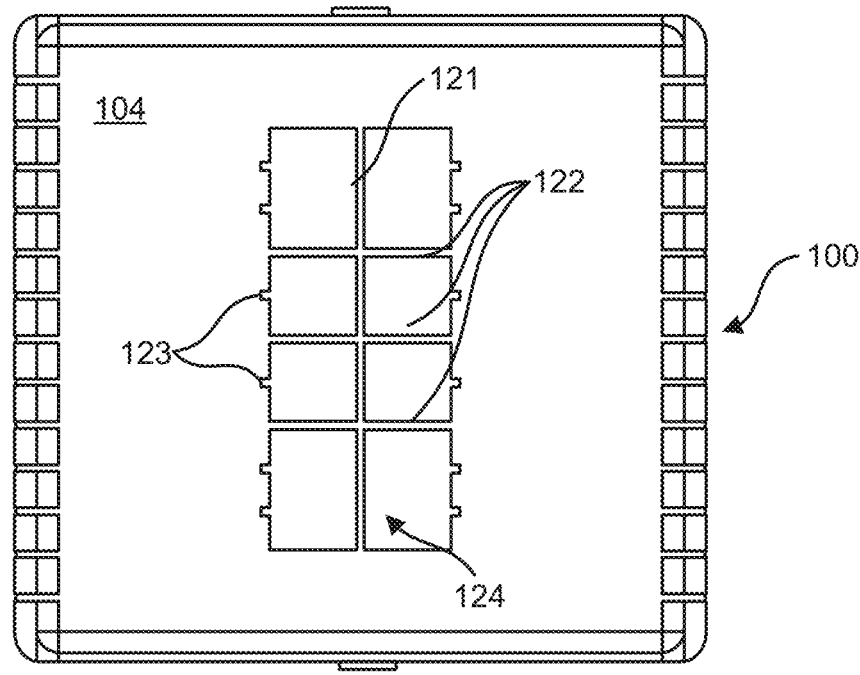
FIG. 1C illustrates a top view of the primary sample holder of FIG. 1A, which includes a grid in the bottom surface of the device that can be used to align the cerebral hemisphere sample along an anterior-posterior commissure line visible on the mesial surface of the brain.
Figure 1D:
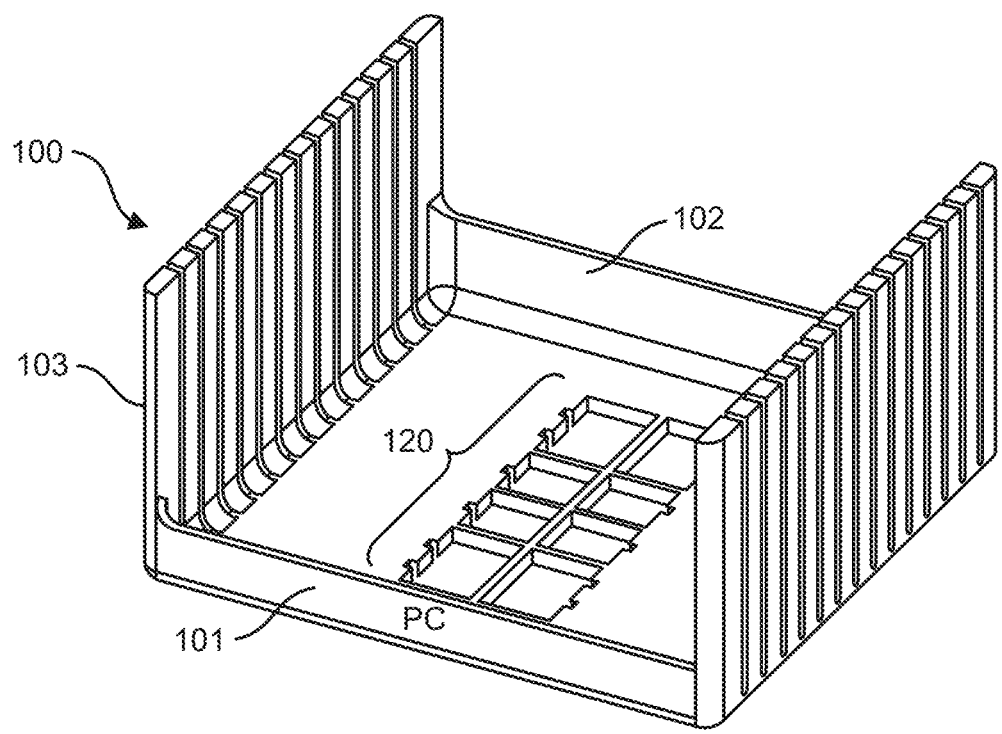
FIG. 1D illustrates a perspective view of the primary sample holder of FIG. 1A.
Figure 2:
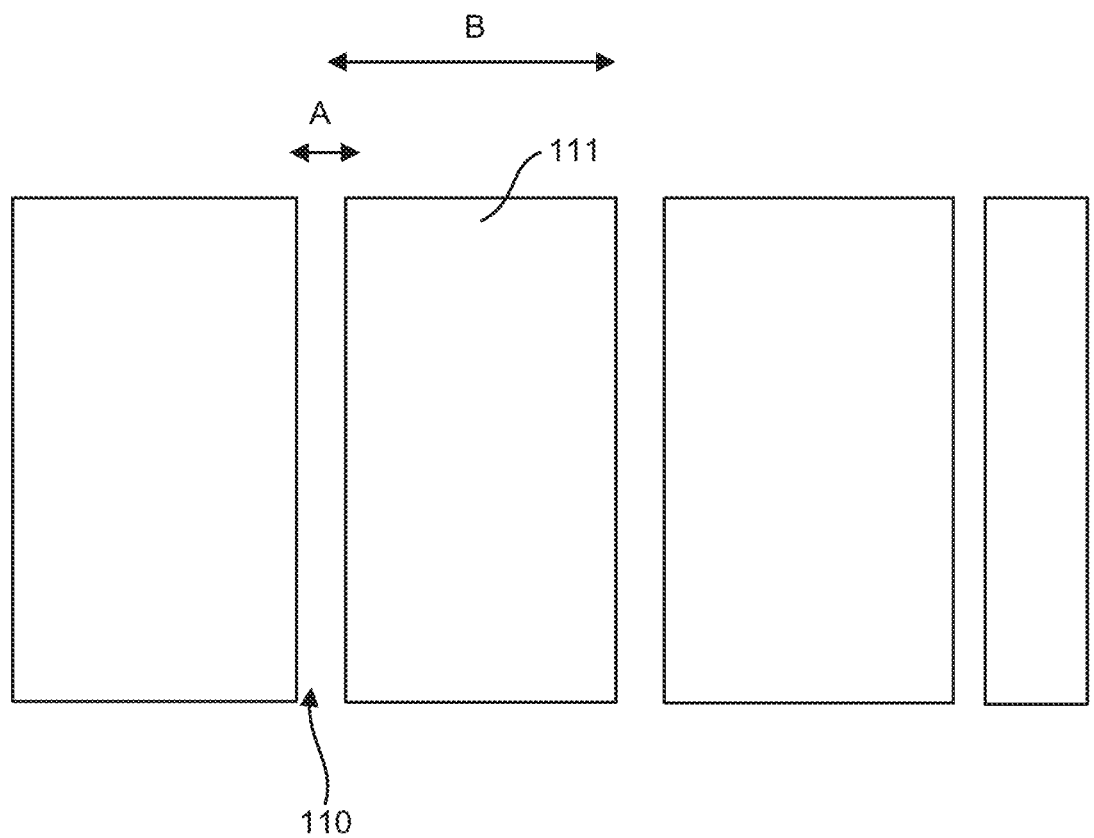
FIG. 2 is a zoomed-in image of a rectangular section of the side wall of the primary sample holder of FIG. 1B. The width "A" can be varied to allow for the profile of different blades or devices for cutting the biological sample. The width "B" can be varied to vary the thickness of the slices that result from cutting. The width of B could also vary moving across the length of the side wall to reproduce different anatomic coordinate systems (e.g., the variable spacing present in the standardized Talaraich space for brain slices).

Referring to FIGS. 1A-1D, the primary sample holder 100 is configured for imaging, transporting, and cutting the biological sample 400 without movement and with consistent, exact stereotactic coordinates. As seen in FIG. 1D, the primary sample holder 100 includes a front wall 101, a back wall 102, side walls 103 positioned between the front wall 101 and the back wall 102, and bottom wall 104. The front wall 101 and the back wall 102 may be labeled to indicate the anterior and posterior, respectively, to assist with consistent orientation of the biological sample 400. The side walls 103 include a plurality of slots 110 spaced at equal, predetermined distances/intervals from one another. The slots 110 extend from a top of the side wall 103 to a bottom of the side wall 103. Referring to FIG. 2, a zoomed-in illustration of a side wall 103, the slots 110 divide the side wall 103 into a plurality of sections 111. As seen in FIG. 1B, each of the sections 111 may be labeled with a number (e.g., 1-14 in the example of FIG. 1B) for naming individual slices of the biological sample. The same number of slots 110 and sections 111 are provided on each of the side walls 103. The slots 110 and the sections 111 of a first side wall 103 align with the slots 110 and the sections 111 of a second side wall 103. Note the designation of front, back and side walls is for the purposes of describing an illustrative embodiment of the invention, but the concepts described herein are not limited in this regard. In other embodiments, more than two walls or all of the walls can have slots or be labeled in whatever manner suits the application. In the illustrated embodiment, the front and back walls are lower to facilitate fluid movement, but the concepts described herein are not limited in this regard. In other embodiments, the heights of the walls can be uniform or vary with respect to one another, depending on the height of the biological sample (tissue/organ) to be imaged and later cut.

Figure 3A:
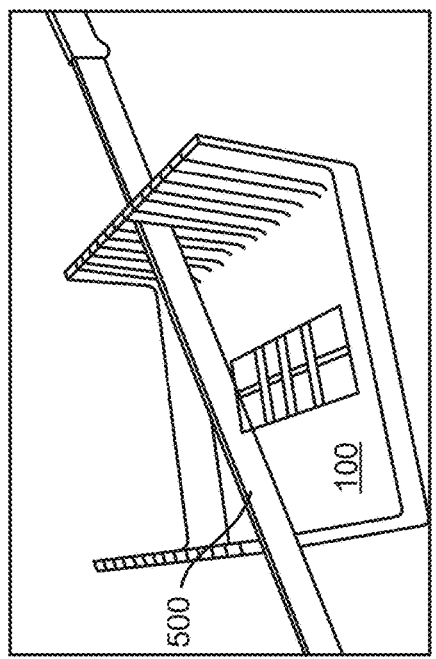
FIG. 3A illustrates the primary sample holder of FIG. 1A with a cutting device for cutting slices of the biological sample. The grid in the bottom of the primary sample holder is for aligning the biological sample with the anterior-posterior commissure plane.
Figure 3B:
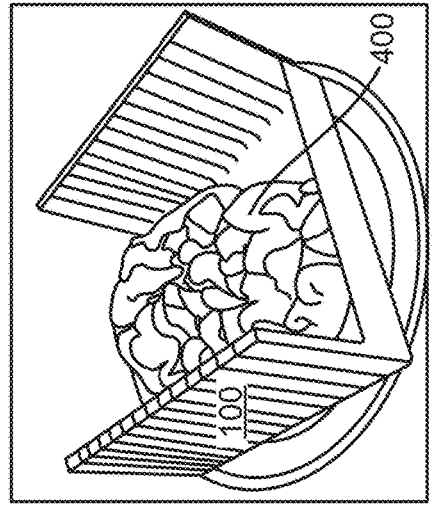
FIG. 3B illustrates a cerebral hemisphere as the biological sample in the primary sample holder of FIG. 1A.
Figure 3C:
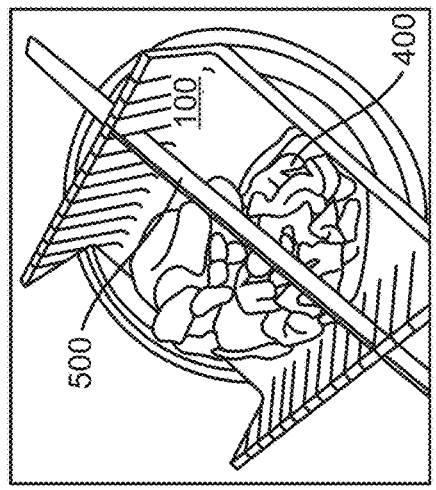
FIG. 3C illustrates how the cerebral hemisphere of FIG. 3B would be cut into slices with a cutting device.

Referring to FIGS. 3A-3C, the slots 110 are configured to receive a cutting device 500 for cutting the biological sample 400 into slices of consistent thickness. The cutting device 500 may be, for example, a non-serrated (smooth) blade, a wire, a laser or the like. Each of the slots 110 has a width A, and each of the sections 111 has a width B (see FIG. 2). The slots 110 are oriented to provide coronal, axial, sagittal or specific oblique cutting orientations relative to an anterior-posterior commissure plane. The width A of the slots 110 can be varied to accommodate the size/shape of the cutting device 500. The width B can be varied to change the thickness of the slices of the biological sample 400 that result from cutting with the cutting device 500. In some examples, each of the sections 111 has a same width B. In other examples, the width of the sections can vary across the width of the side wall 103 to reproduce different anatomic coordinate systems, depending on the type of biological sample 400 being analyzed. For example, the width of the sections 111 may be widened as the distance from the center cut (at the center of the side wall 103) increases to reproduce Talairach coordinate slices when cutting a brain.

The bottom wall 104 includes a grid 120 configured to assist in aligning the biological sample 400 received in the primary sample holder 100. The grid 120 may be a hole 124 in the bottom wall 104 bisected by a central panel 121 that runs along a longitudinal axis of the primary sample holder 100. The central panel 121 may be intersected by a plurality of axial panels 122 along a length thereof to form the grid 120. A thickness or height of the central panel 121 and the axial panels 122 is the same as a thickness or height of the bottom wall 104. A top surface of the grid 120 is flush with a top surface of the bottom wall 104 (i.e., the grid 120 does not protrude from the top surface of the bottom wall 104). The central panel 121 and the axial panels 122 are fiducial markers to assist in positioning the biological sample 400 such that it has the same orientation each time and the same relative orientation as other biological samples of the same type, with respect to the planes of imaging and cutting. The sections formed by the intersection of the central panel 121 and the axial panels 122 may have equal dimensions (not illustrated), or the sections may have varying dimensions (see FIG. 1C). The thickness and number of slices will depend on the intended application, and the size and geometry of the biological sample 400. In an example in which the biological sample 400 is a brain, a user would utilize the central panel 121 to align the whole brain or the hemisphere of the brain along the anterior-posterior commissure line, as routinely done with imaging. Because the grid 120 (i.e., the fiducial markers) are located on the bottom wall 104 of the primary sample holder 100, the grid 120 may be visualized by elevating the primary sample holder 100 with the biological sample 400 held therein, or by holding the primary sample holder 100 with the biological sample 400 held therein over a mirror.

A plurality of notches 123 may be provided along an exterior perimeter of the hole defining the grid 120. The notches 123 are aligned with the slots 110 in the side walls 103 to aid recognition of where the cuts would occur when positioning the biological sample 400 within the primary sample holder 100.

FIG. 3A illustrates the primary sample holder 100 with the cutting device 500 inserted in one slot 110 of the first side wall 103 and one slot 110 of the second side wall 103. As seen in FIG. 3A, in some uses, the cutting device 500 is not received in slots 110 of the side walls 103 that are directly opposite to and aligned with one another. As seen in FIG. 3C, however, in some uses, the cutting device 500 is received in slots 110 of the side walls 103 that are directly opposite to and aligned with one another. The slots 110 selected to receive the cutting device 500 depend on the desired angle/orientation of the slice of the biological sample 400. In FIGS. 3B and 3C, the biological sample 400 is a cerebral hemisphere (half brain). In FIG. 3B, the cerebral hemisphere has been aligned with the anterior-posterior commissure plane before imaging is performed with the assistance of the grid 120. FIG. 3B shows the cerebral hemisphere in the primary sample holder 100 prior to immersion in liquid for imaging. FIG. 3C demonstrates how the cerebral hemisphere may be sliced after imaging is complete to maintain exact stereotaxis with the imaging data. In the example of FIGS. 3A-3C, the width B of the sections 111 is 1 cm, so each coronally-cut slice would be 1 cm thick.

The primary sample holder 100 is configured to hold the biological sample 400 in a stable position so that the biological sample 400 does not move during or between the medical imaging and sample cutting procedures. The marked front wall 101, back wall 102, and side walls 103, as well as the grid 120, facilitate returning the biological sample 400 to the original position should movement of the biological sample 400 be required or inadvertently occur.

This stable position can be prescribed, obtained and reproduced for the individual biological sample 400, or the same relative stable position can be prescribed, obtained and reproduced for a plurality of biological samples 400 of the same type (e.g., a plurality of brains for pathological analysis).

In general, once placed in the primary sample holder 100, the biological sample 400 does not move due to gravity and the weight of the biological sample 400. In some examples, a bag containing water or another high permittivity fluid may be placed on top of the biological sample 400 to weigh down the biological sample 400 and hold the biological sample 400 in place.

The primary sample holder 100 can be adapted for use with a biological sample of any shape or size. In some examples, the side walls 103 are stationary. In other examples, the side walls 103 may be configured to translate, to telescope to adjust a height thereof, and/or to pivot. For example, the side walls 103 may be configured to reversibly and repeatedly translate or slide inwards and outwards with respect to the longitudinal axis of the primary sample holder 100 to confine the biological sample 400 more carefully and keep it in a centered position on the bottom wall 104 of the primary sample holder 100. The entire side wall 103 may be translated inwards or outwards, or individual sections 111 of the side wall 103 may be translated inwards or outwards. For example, if the primary sample holder 100 was 15 cm wide, and the biological sample 400 was 12.4 cm wide and oriented along the anterior-posterior commissure line, there would be a 1.3 cm wide gap on either side of the biological sample 400. In this situation, the side walls 103 could be slid inwards to appose the edges of the biological sample 400. This would facilitate more exact cutting and stereotaxis of the biological sample 400 during the cutting procedure that follows medical imaging of the biological sample 400.

Instead of or in addition to being able to slide inwards and outwards, the side walls 103 may also be configured to pivot to adjust the angle of cutting for corrections relative to the anterior-posterior commissure line. The entire side wall 103 may be pivoted, or individual sections 111 of the side wall 103 may be pivoted. For example, in a given whole brain sample, this line will not be visible on the surface of the biological sample and may need to be identified with imaging. An MRI or CT visible fiducial could be placed on the side of the primary sample holder 100 to measure the angle for correction to the anterior-posterior commissure line or plane during imaging and this angle may then be used for the constructed pivot so that cuts are made as desired.

In some examples, the side walls 103 may be telescopic such that a height of the side walls 103 may be adjusted. The height of the side walls 103 may be adjusted over any suitable range, for example, to adjust the height to a value from 6 cm to 8 cm to accommodate a specific size of a biological sample 400, while minimizing the field-of-view for imaging to help the user improve signal to noise and/or spatial resolution of the image. The entire side wall 103 may be telescopic, or individual sections 111 of the side wall 103 may be telescopic. The telescoping side walls 103 may further be configured to slide and/or pivot as described above.

Although not illustrated in FIGS. 1A-1D, in some examples, the primary sample holder 100 may include a top wall (i.e., a lid). The top wall may be secured to gently hold the top of the biological sample 400 in position (via compression), prevent stress on the side walls 103, prevent splashing or spillage of liquid or biological material, protect (and hide) the biological sample, and/or prevent movement of the biological sample 400 during imaging and transportation. Like the side walls 103, the top wall can be labeled to facilitate stereotaxis throughout the medical imaging and pathological analyses. In some examples, the top wall may be removed when it is time to cut the biological sample 400, while in other examples, the top wall may remain as part of the overall primary sample holder 100 and allow entry of the cutting device 500 below the "roof" of the primary sample holder 100. In additional examples, the top wall of the primary sample holder 100 may be mobile and adjustable, for example, configured to reversibly and repeatedly translate upwards and downwards to confine the biological sample 400 more closely so that movement is less likely. For example, the top wall may be configured to translate upwards and downwards on columns placed just inside the corners of the primary sample holder 100 (defined by the front wall 101, the back wall 102, and the side walls 103) or inserted into cut inserts within the inner corners of the primary sample holder 100 (defined by the front wall 101, the back wall 102, and the side walls 103) such that the top wall can slide down on the biological sample's superior surface within the primary sample holder 100, while maintaining a horizontal plane.

Although not illustrated, in some examples, the front wall 101 and the back wall 102 may include a plurality of slots similar to the slots 110 of the side walls 103. Provision of slots in the front wall 101 and the back wall 102 would allow the biological sample 400 to be cut in two planes, while held in the primary sample holder 100.

In some examples, the side walls 103 may be removable and interchangeable such that versions could be used to hold the biological sample 400 in position during imaging and/or transportation, but then replaced by side walls having slots with a custom spacing between adjacent slots, where spacing depend on the individual biological sample 400. Further, the biological sample 400 could be imaged in a primary sample holder 100 having a standard shape and size, and then side walls specifically 3D printed for cutting that exactly reproduces desired divisions in biological sample 400 (e.g., divisions in the Talairach space of a brain).

In other examples, the width B of the sections 111 (see FIG. 2) may be very small such that there is a large number of slots 110 on each side wall 103 configured to receive the cutting device 500. After imaging is completed, only certain slots 110 having width A are used to cut the biological sample, potentially using one of the coordinate systems described above, but without requiring specific side walls to be created specifically for the individual biological sample. Such cutting could be regular and multiples of gaps, or be specific to the location within the overall biological sample (e.g., for recapitulating Talaraich coordinates). In this example, the individual sections 111 may be made taller than surrounding pieces every 5 mm, 10 mm or other predetermined distance to facilitate equal cutting when standard pathological cutting is desired. Cuts could also be proscribed at certain positions based on the imaging obtained prior to cutting the biological sample to localize a particular tissue feature or structure of interest.

For MRI imaging, the biological sample 400 will be imaged while submerged in a solution such as water, chemical fixative (e.g., formalin, formaldehyde, glutaraldehyde or some mixture thereof), phosphate buffer or susceptibility matched fluid (such as Fomblin or Fluroinert). In CT or other modalities of imaging, the biological sample 400 will also be maintained in a wet environment to prevent tissue desiccation and/or damage. The primary sample holder 100 is configured to tolerate this immersion in liquid and also configured to drain the liquid (when desired) without moving the biological sample 400.

Figure 11A:
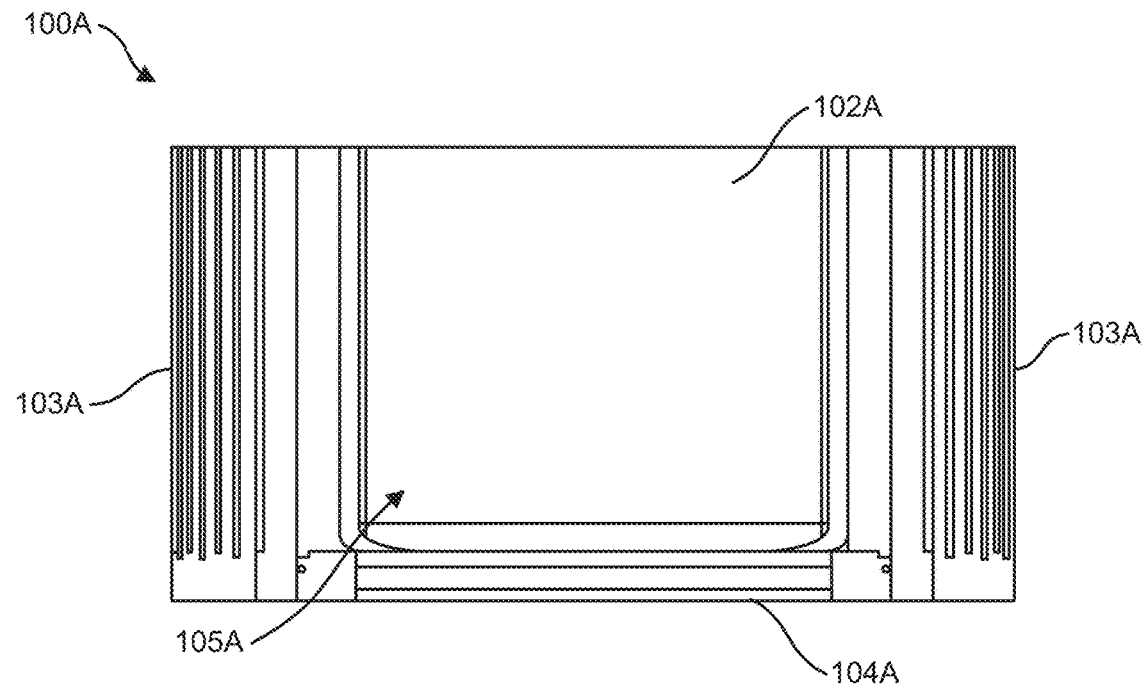
FIG. 11A illustrates another embodiment of a primary sample holder from a front view.
Figure 11B:
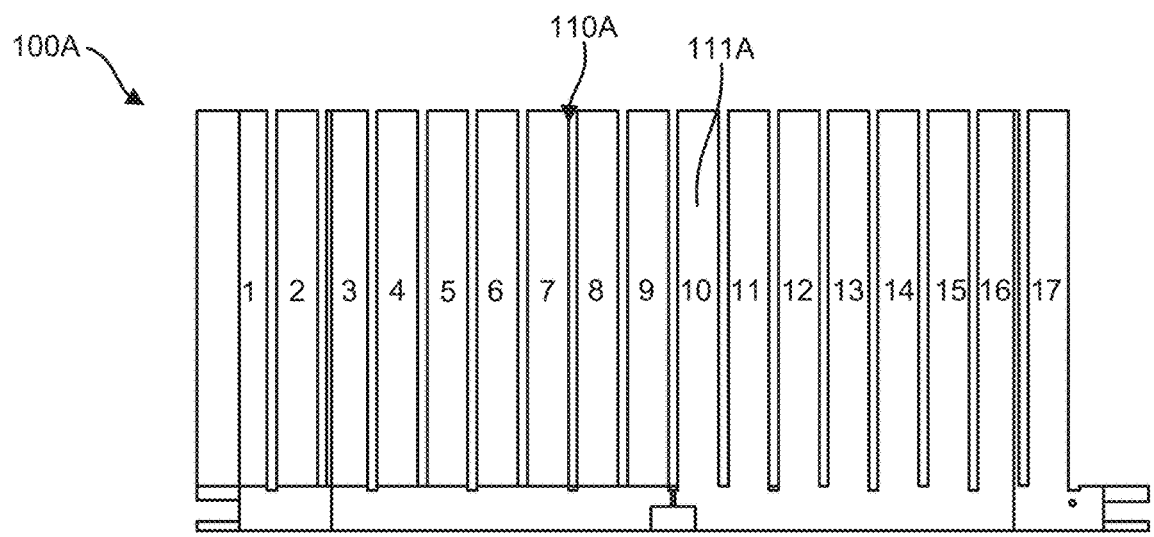
FIG. 11B illustrates the primary sample holder of FIG. 11A from a side view.
Figure 11C:
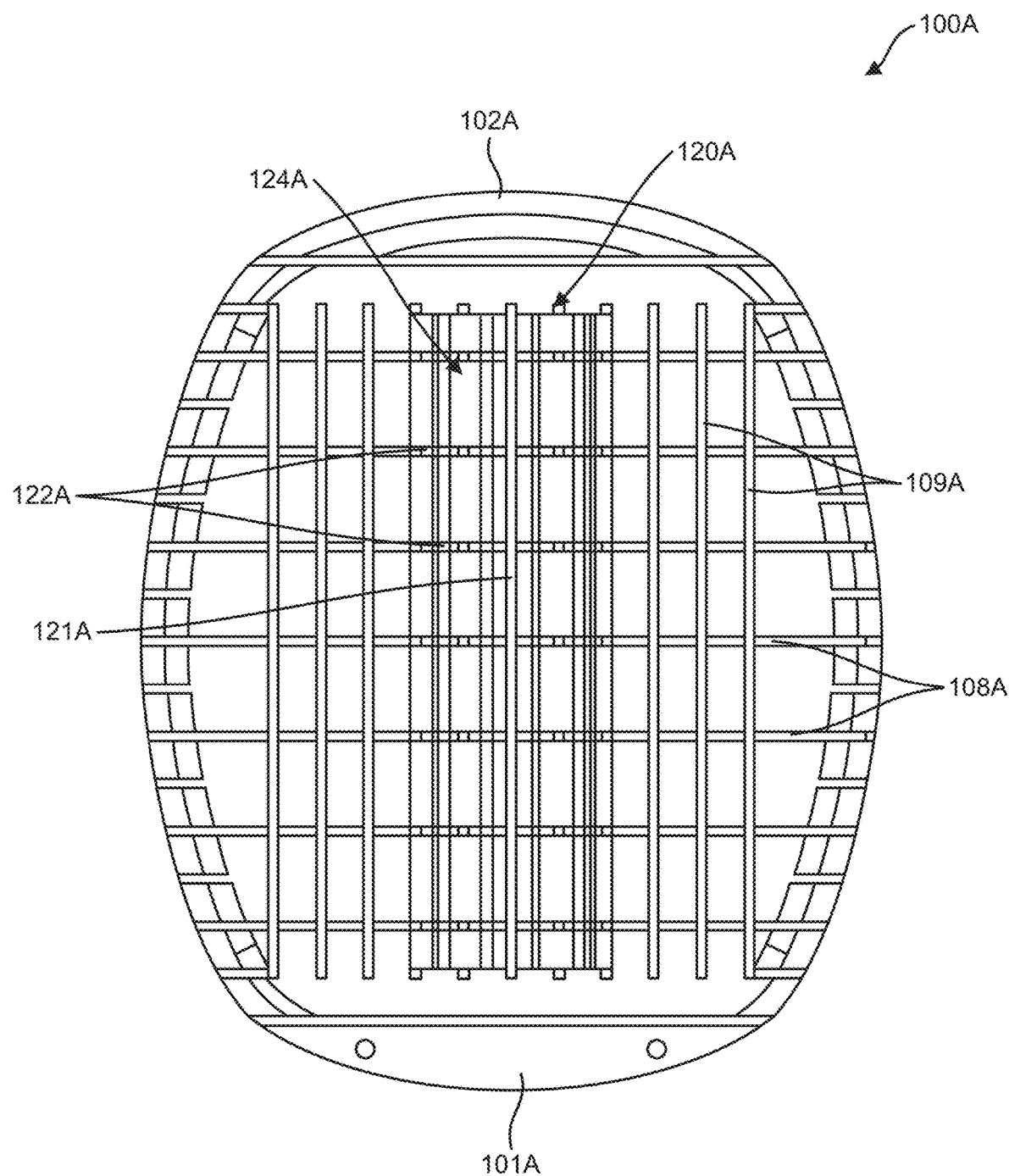
FIG. 11C illustrates the primary sample holder of FIG. 11A from a top view.

FIGS. 11A-11C illustrate an alternative embodiment of a primary sample holder 100A that can be used instead of the primary sample 100 described above the primary sample holder 100 for imaging, transporting, and cutting the biological sample 400 without movement and with consistent, exact stereotactic coordinates. Thus, the primary sample holder 100A may be interchangeable with the primary sample holder 100 described above. As seen in FIG. 11A, a front side 101A of the primary sample holder 100A has an opening 105A to facilitate placing the biological sample 400 within the primary sample holder 100A. A back side 102A (opposite to the front side 101A) is a solid wall. Like the primary sample holder 110, the side walls 103A (positioned between the front side 101A and the back side 102A) include a plurality of slots 110A spaced at equal, predetermined distances/intervals from one another. The slots 110A extend from a top of the side wall 103A to a bottom of the side wall 103A. As seen in FIG. 11B, the slots 110A divide the side wall 103A into a plurality of sections 111A. Each of the sections 111A may be labeled with a number (e.g., 1-17 in the example of FIG. 11B) for naming individual slices of the biological sample. The same number of slots 110A and sections 111A are provided on each of the side walls 103A. The slots 110A and the sections 111A of a first side wall 103A align with the slots 110A and the sections 111A of a second side wall 103A. The heights of the side walls 103A and the solid wall at the back side 102A can be uniform or vary with respect to one another, depending on the height of the biological sample (tissue/organ) to be imaged and later cut.

The slots 110A are configured to receive a cutting device 500 for cutting the biological sample 400 into slices of consistent thickness. The cutting device 500 may be, for example, a non-serrated (smooth) blade, a wire, a laser or the like. Similar to the illustration in FIG. 2, each of the slots 110A has a width A, and each of the sections 111A has a width B. The slots 110A are oriented to provide coronal, axial, sagittal or specific oblique cutting orientations relative to an anterior-posterior commissure plane. The width A of the slots 110A can be varied to accommodate the size/shape of the cutting device 500. The width B can be varied to change the thickness of the slices of the biological sample 400 that result from cutting with the cutting device 500. In some examples, each of the sections 111A has a same width B. In other examples, the width of the sections can vary across the width of the side wall 103A to reproduce different anatomic coordinate systems, depending on the type of biological sample 400 being analyzed. For example, the width of the sections 111A may be widened as the distance from the center cut (at the center of the side wall 103A) to reproduce Talairach coordinate slices when cutting a brain.

The bottom wall 104A includes a grid 120A configured to assist in aligning the biological sample 400 received in the primary sample holder 100A. The grid 120A may be a hole 124A in the bottom wall 104A bisected by a central panel 121A that runs along a longitudinal axis of the primary sample holder 100A. The central panel 121A may be intersected by a plurality of axial panels 122A along a length thereof to form the grid 120A. In FIG. 11C, there are additional bars in the grid 120A at the floor of the primary sample holder 100A, which represent the overhead appearance of the fiducial letters for stereotaxis in the floor or bottom wall 104A of the primary sample holder 100A and provide further strength to the bottom of the primary sample holder 100A. A thickness or height of the central panel 121A and the axial panels 122A is the same as a thickness or height of the bottom wall 104A. A top surface of the grid 120A is flush with a top surface of the bottom wall 104A (i.e., the grid 120A does not protrude from the top surface of the bottom wall 104A). The central panel 121A and the axial panels 122A are fiducial markers to assist in positioning the biological sample 400 such that it has the same orientation each time and the same relative orientation as other biological samples of the same type, with respect to the planes of imaging and cutting. The sections formed by the intersection of the central panel 121A and the axial panels 122A may have equal dimensions, or the sections may have varying dimensions. The thickness and number of slices will depend on the intended application, and the size and geometry of the biological sample. In an example in which the biological sample 400 is a brain, a user would utilize the central panel 121A to align the whole brain or the hemisphere of the brain along the anterior-posterior commissure line, as routinely done with imaging. Because the grid 120A (i.e., the fiducial markers) are located on the bottom wall 104A of the primary sample holder 100A, the grid 120A may be visualized by elevating the primary sample holder 100A with the biological sample 400 held therein, or by holding the primary sample holder 100A with the biological sample 400 held therein over a mirror.

The bottom wall 104A of the primary sample holder 100A may include grooves 108A that are parallel with respect to one another, and extend in a direction from a first side wall 103A to a second side wall 103A. The grooves 108A are indentations in the bottom wall 104A that are aligned with some or all of the slots 110A to allow the cutting device 500 to go beyond the floor in the same plane as the slots 110A. The bottom wall 104A may include additional grooves 109A that are parallel with respect to one another, and extend in a direction from the front side 101A to the back side 102A. The additional grooves 109A are oriented vertically in the image and may be aligned with labels on the bottom wall or the front side (e.g., letters A-I on the front side of FIG. 11A) to allow for precise stereotaxis in a second plane. Horizontal notches in the internal edges of the sections 111A allow for precise stereotaxis in a third dimension. These notches correspond to gaps in the secondary holder as shown in other figures. Although not illustrated, one of ordinary skill in the art would understand that the primary sample holder 100 of FIGS. 1A-1D may include grooves similar to the grooves 108A and 109A, as well as notches in the internal edges of the sections 111.

Secondary Sample Holder

Referring to FIGS. 4A-4D, the secondary sample holder 200 includes a front wall 201, a back wall 202, side walls 203, and a bottom wall 204. In the illustrated embodiment, the front wall 201, the back wall 202, and the side walls 203 have the same height, but the concepts described herein are not limited in this regard. In other embodiments, the heights of the walls can be uniform or vary with respect to one another, depending on the height of the biological sample (tissue/organ) to be imaged and later cut. Each of the front wall 201, the back wall 202, and the side walls 203 include a plurality of slots 210 spaced at equal, predetermined distances/intervals from one another. The slots 210 extend from a top of the side wall 203 to a bottom of the side wall 203. Referring to FIG. 5, a zoomed-in illustration of any one of the front wall 201, the back wall 202, or the side walls 203, the slots 210 divide the wall into a plurality of sections 211. The same number of slots 210 and sections 211 are provided on each of the side walls 203. The slots 210 and the sections 211 of a first side wall 203 align with the slots 210 and the sections 211 of a second side wall 203. The same number of slots 210 and sections 211 are provided on each of the front wall 201 and the back wall 202. The slots 210 and the sections 211 of the front wall 201 align with the slots 210 and the sections 211 of the back wall 202. In some examples, the side walls 203 have the same number of slots 210 and sections 211 as the front wall 201 and the back wall 202. In other examples, the side walls 203 have a different number of slots 210 and sections 211 as the front wall 201 and the back wall 202. Each of the slots 210 has a width C, and each of the sections 211 has a width D (see FIG. 5). As described above with respect to the primary sample holder 100, the front wall 201, the back wall 202, and the side walls 203 as a whole, or individual sections 211 of the front wall 201, the back wall 202, and the side walls 203 may be configured to reversibly and repeatedly translate inwardly and outwardly, telescope to adjust a height thereof, of pivot.

Figure 4A:
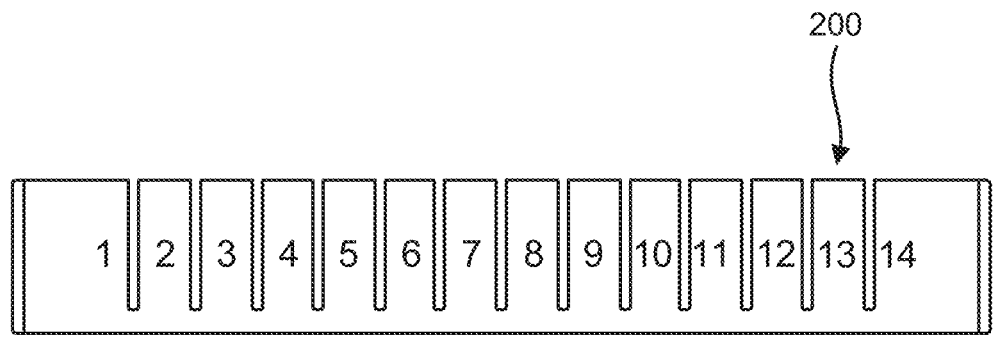
FIG. 4A illustrates a secondary sample holder for cutting a slice of the biological sample obtained from cutting the biological sample in the primary sample holder of FIG. 1 into a smaller sample size. This holder is designed to enable precise cutting of the biological sample in the two additional planes that are orthogonal to the cutting plane in the first holder.
Figure 4B:
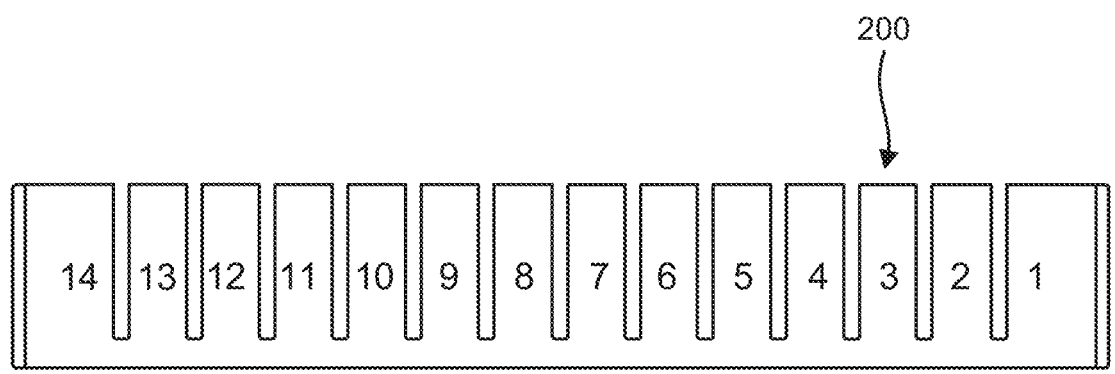
FIG. 4B is side view of the secondary sample holder of FIG. 4A.
Figure 4C:
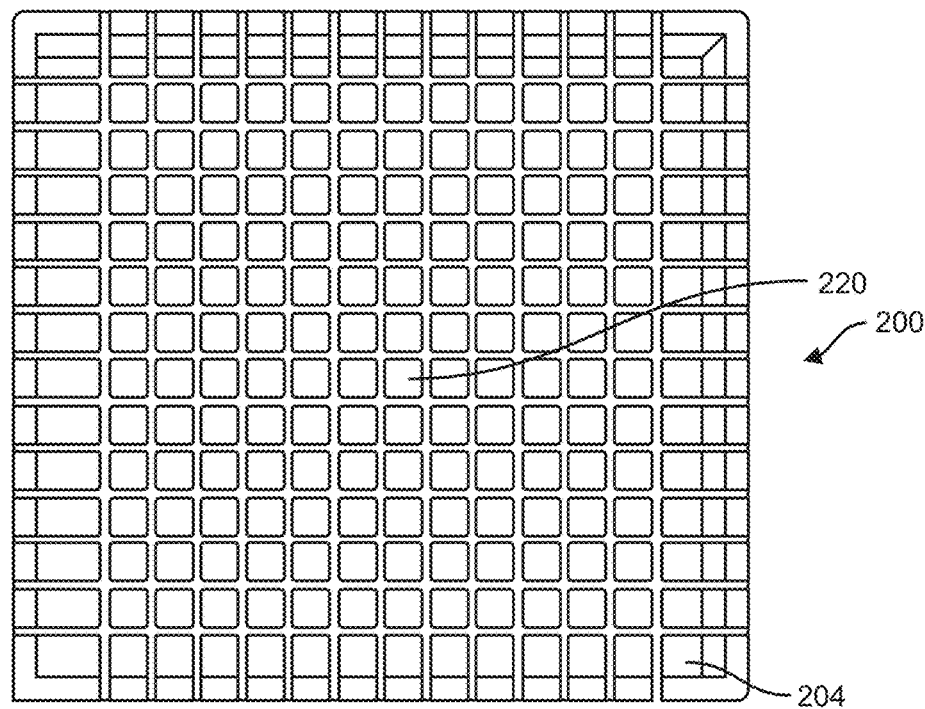
FIG. 4C is a top view of the secondary sample holder of FIG. 4A. The grid-like pattern is comprised of small linear indentations in the bottom wall or floor of the secondary sample holder to allow a cutting device to pass cleanly through the slice of the biological sample.
Figure 4D:
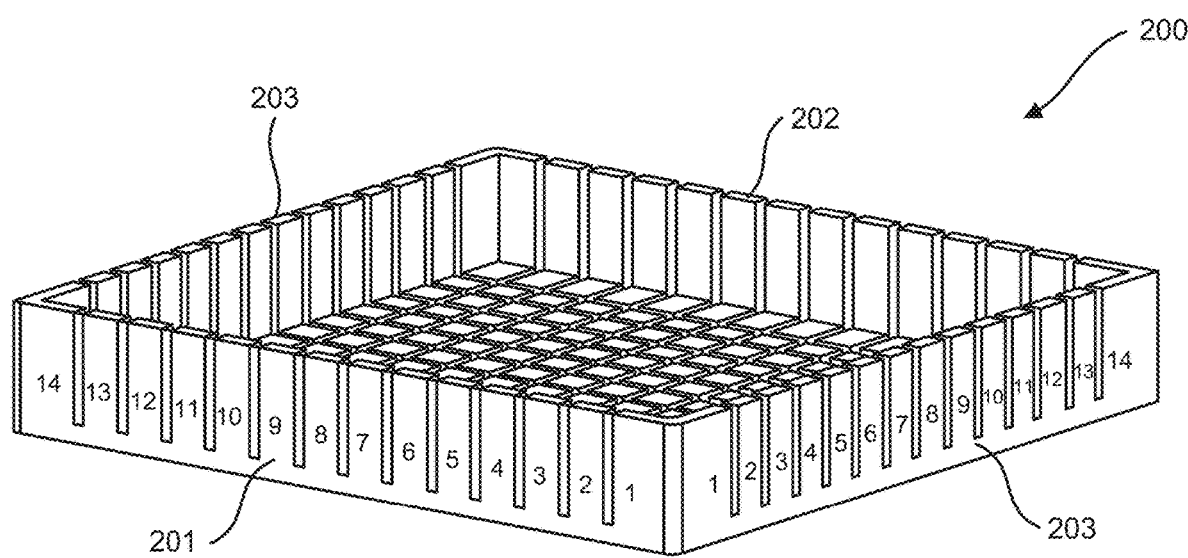
FIG. 4D is a perspective view of the secondary sample holder of FIG. 4A.
Figure 5:
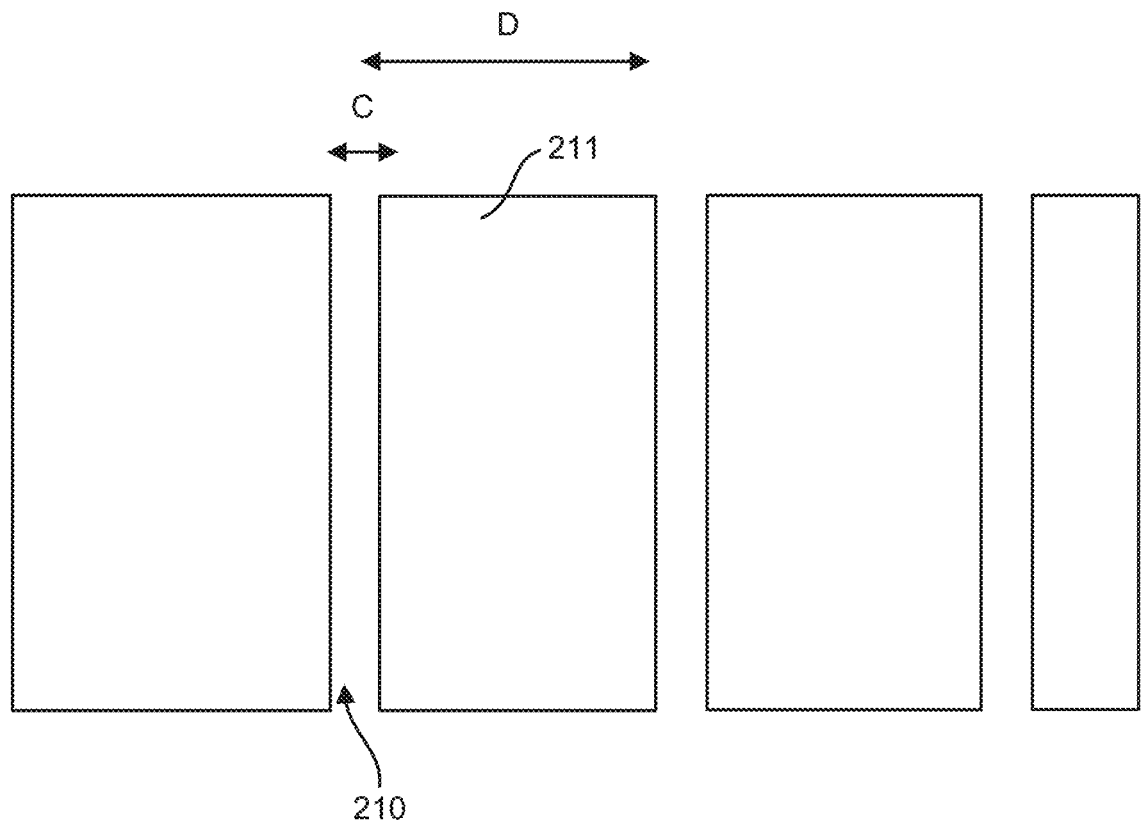
FIG. 5 is a zoomed-in image of a rectangular section of the side wall of the secondary sample holder of FIG. 4A. The width "C" can be varied to allow for the profile of different blades or devices for cutting the biological sample. The width "D" can be varied to vary the thickness of the slices that result from cutting. The width of D could also vary moving across the length of the side wall to reproduce different anatomic coordinate systems.

As seen in FIGS. 4A, 4B and 4D, each of the sections 211 may be labeled with a number (e.g., 1-14) for naming individual slices of the biological sample. At least one of the front wall 201, the back wall 202 or the side walls 203 may be labeled to present the bottom wall 104 of the primary sample holder 100 so that the slice of the biological sample 400 obtained from the primary sample holder 100 may be moved in direct contact with the wall to exactly reproduce the slice orientation in the primary sample holder 100. In the initial embodiment of the primary sample holder, cuts are only made in the coronal plane. The floor of the primary sample holder however can have grooves that run orthogonal to the coronal planes for cutting created by the gaps in the sidewalls. Between these grooves, labels such as "A", "B" or other ordering nomenclature can be used (similar to the sidewalls). Labels and the grooves in the floor of the primary holder will be visible to all imaging modalities. When the tissue slice is removed from the primary sample holder and placed flat in the secondary holder, these floor grooves will correspond exactly to the gaps in two opposing walls as long as the slice is positioned correctly—new cuts in this second plane can then be used to isolate the area of interest with stereotactic precision relative to the previous imaging. An analogous situation can be created in the third dimension by putting notches in the sidewalls at various heights above the floor of the primary holder device.

As seen in FIG. 4C, the secondary sample holder 200 includes a grid 220 made of a plurality of linear indentations in the bottom wall 204 of the secondary sample holder 200. The indentations allow the cutting device 500 to pass cleanly through the biological sample 400.

The secondary sample holder 200 is configured to receive and hold a slice of the biological sample 400 that was cut from the biological sample 400 while held in the primary sample holder 100. Referring to the example of FIG. 3C, a slice cut from the biological sample 400 while held in the primary sample holder 100 would be a coronal slice. The coronal slice would then be laid flat in the secondary sample holder 200 and aligned with one of the front wall 201, the back wall 202, or the side walls 203 so that the stereotactic coordinates in the primary sample holder 100 are reproduced in the secondary sample holder 200. The coronal slice can then be cut in one or two additional planes by the cutting device 500. For example, if the width B of the sections 111 of the primary sample holder 100 is 1 cm, and the width D of the sections 211 of the secondary sample holder 200 is also 1 cm, additional cuts in two planes using the secondary sample holder 200 would result in 1 cm cubic samples of the biological sample 400 with precise stereotactic localization relative to the image obtained when the biological sample 400 was imaged in the primary sample holder 100.

The samples (e.g., the 1 cm cubic samples of the biological sample 400) obtained from cutting within the secondary sample holder 200 may be imaged within the secondary sample holder 200 or stored in a storage container configured to keep the slice orientation and order correct. The storage container may have individual slots for tissue slices of specific or generic dimensions. Gaps between slices could be varied so that samples are kept separate. Often the gap will be minimal to reduce the overall field-of-view that is required for imaging all the samples. The slots for individual slices may be, for example, wells configured to accommodate fluid immersion of the slices. This storage container may also include fiducials along the front wall, back wall, side walls, bottom wall, and/or top wall of the slots for stereotaxis. The storage container may be manufactured of any suitable material. The storage container may be, for example, translucent for visual inspection and verification of slices and stereotaxis.

Once the initial slices are cut from the primary sample holder 100, the slices may need to be stored prior to further study or cutting. A supplementary holder can be designed to hold these brain slices together in the correct original orientation or with slight separations. The slices will be immersed in the appropriate fluid to prevent dehydration (creating individual wells for individual slices). The design also lends itself to imaging the tissue (either in a repeat manner or potentially as the first time the slices can be imaged. Within these individual wells, there can also be fiducial markers for the edges of the sample to create stereotaxis if the individual slices are to be cut later using a different device in the other two planes (such as the secondary sample holder 200)

If even smaller sample sizes are desired (e.g., fine 1-2 mm thick sample sizes), the sample obtained from the secondary sample holder 200 (e.g., the 1 cm cubic sample) can be placed in a tertiary sample holder that is a smaller, scaled down version of the secondary sample holder 200 for even stereotactic localization of the correct tissue (using a finer cutting device 500 and slots having a width smaller than the width C of FIG. 5).

Outer Shell

The outer shell 300 has three primary purposes—1) to contain the primary sample holder 100, the biological sample 400, and the immersion liquid, 2) to facilitate fit to the imaging device (e.g., outer contours matching the MM head coil in FIG. 6C), and 3) to position the biological sample 400 in the ideal location for imaging (e.g., as close as possible to the coil elements for a specific individual coil when performing MM). In other words, the outer shell 300 positions the biological sample 400 in the best position for optimum signal and imaging efficiency with respect to imaging coverage, geometry and time required to complete the scan.

Figure 13:
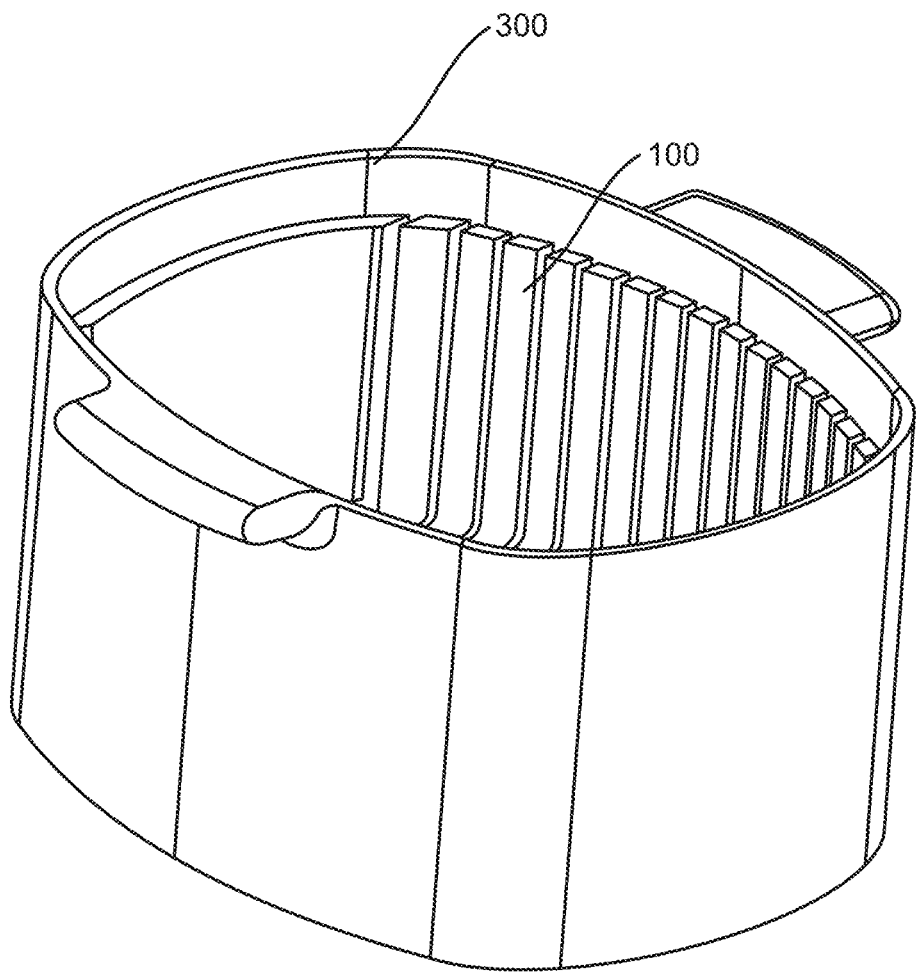
FIG. 13 illustrates a perspective view of the primary sample holder of FIG. 11A placed in the outer shell of FIG. 12A.

Referring to FIGS. 12A-12D, the outer shell 300 is a solid piece for containing the primary sample holder 100 and immersing the biological sample 400 and the primary sample holder 100 in liquid such as water, a phosphate buffer, formaldehyde solution or a susceptibility matching solution. The shape of the outer shell 300 substantially corresponds to a shape of the primary sample holder (e.g., the shape of the outer shell 300 of FIGS. 12A-12D corresponds to the shape of the primary sample holder 100A of FIGS. 11A-11C), but the outer shell has slightly larger dimensions. The outer shell 300 can be a single, integral piece shaped to contain the primary sample holder 100, but with outer contours that fit the dimensions of the imaging device (e.g., the MRI coil shown in FIG. 6C). Alternatively, the outer shell 300 may be comprised of two components—a first component that forms a close shell around the primary sample holder 100, and a second component that holds the first component and fits the outer contours of the imaging device (e.g., the first component (B) and the second component (C) of FIG. 14, which will be described in further detail below). This latter version may make it easier to transport biological samples with liquid. In either embodiment, the outer shell 300 may include at least one handle 301 configured to facilitate transporting the biological sample. The handle 301 is shaped and sized to avoid interference with the primary sample holder 100 or the fit within the imaging device. In FIGS. 12A-12D, two handles 301 are provided on opposing sides of the outer shell 300. Further, the floor (i.e., bottom wall) of the outer shell 300 may include ridges, pegs or other devices configured to keep the floor of the primary sample holder 100 slightly elevated to facilitate the movement of fluid around the biological sample. In other words, there may be a gap between the floor of the outer shell 300 and the primary sample holder 100. This gap may also facilitate the removal of air or gas from the biological sample prior to imaging. The inner wall of the outer shell may include grooves or be curved to facilitate tight apposition to the side walls of the primary sample holder 100. Similar concepts can be applied when the secondary sample holder 200 or supplementary holder are placed in the outer shell 300. FIG. 13 illustrates the primary sample holder 100A of FIG. 11A placed in the outer shell 300 of FIG. 12A.

Figure 6C:
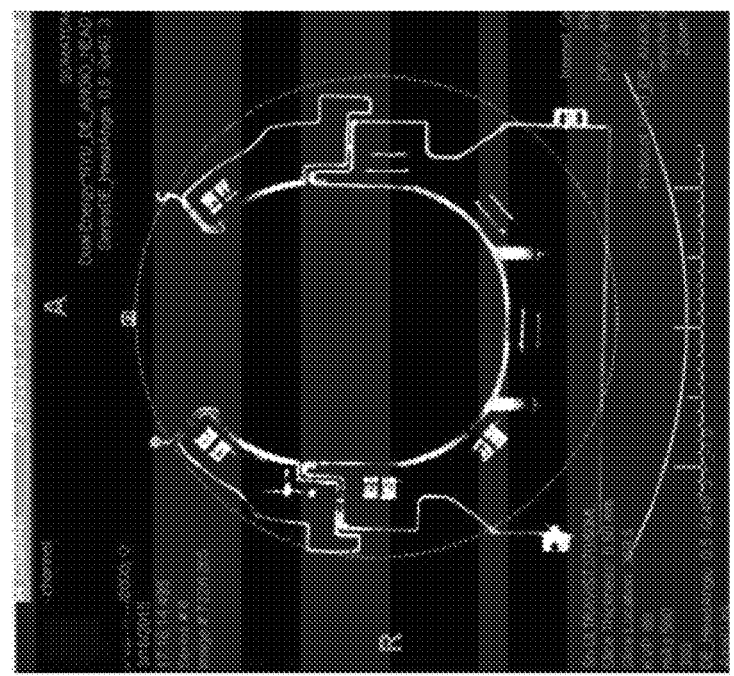
FIG. 6C illustrates that the outer shell can be manufactured to precisely fit inside a specific MRI radiofrequency coil or CT scanner device.
Figure 6B:
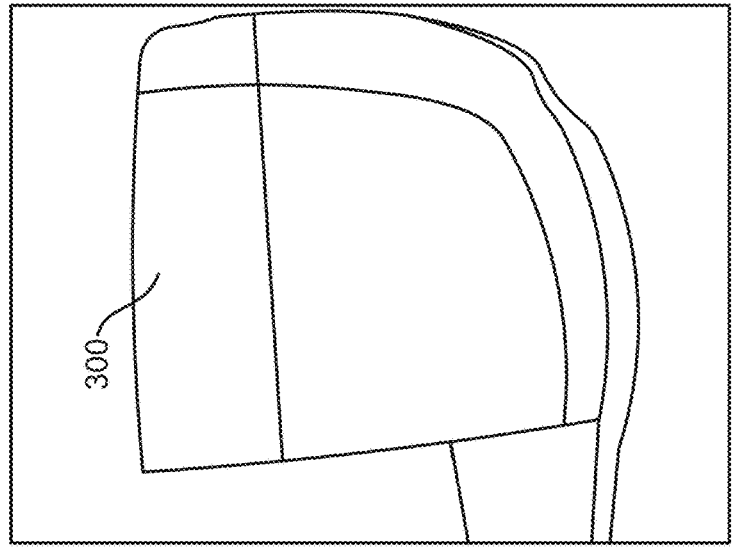
FIG. 6B illustrates a side view of the outer shell of FIG. 6A.
Figure 6A:
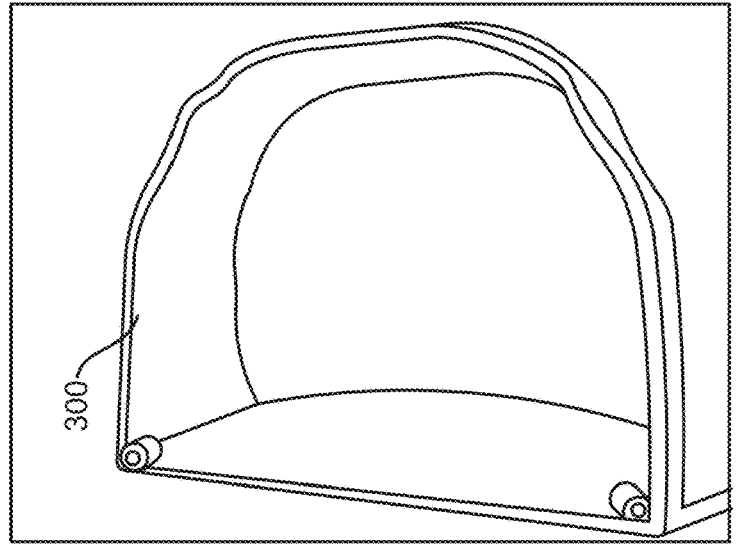
FIG. 6A illustrates a front view of an outer shell configured to hold the primary sample holder of FIG. 1A or the secondary sample holder of FIG. 4A during imaging. The outer shell may serve as a reservoir containing fluid in which the biological sample is immersed during imaging.
Figure 7A:
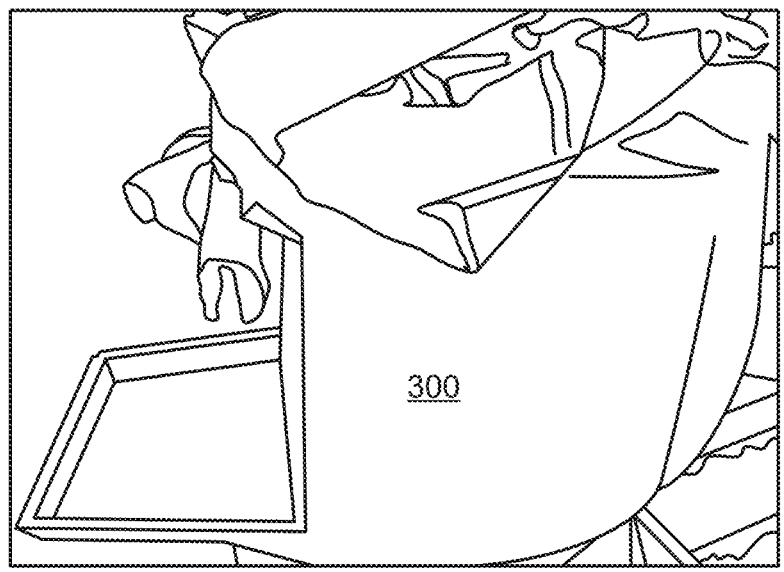
FIG. 7A illustrates a side view of the outer shell of FIG. 6A, including a tray configured to hold the primary sample holder of FIG. 1A or the secondary sample holder of FIG. 4A during imaging. In the illustration, a plastic bag has been used to line an interior of the outer shell, but the plastic bag is not required.
Figure 7B:
FIG. 7B illustrates a front view of the outer shell of FIG. 7A. In the illustration, a plastic bag has been used to line an interior of the outer shell, but the plastic bag is not required.
Figure 7C:
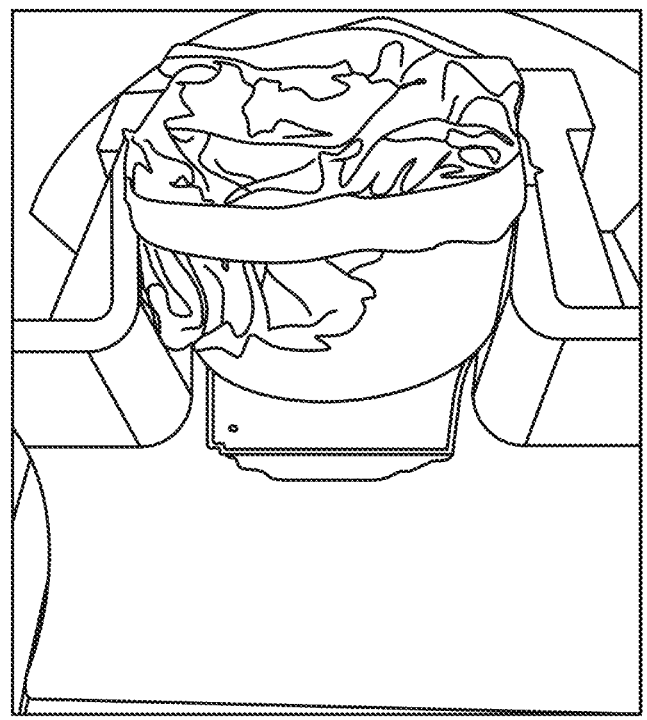
FIG. 7C illustrates the outer shell of FIG. 7A placed within an MIll manufacturer's head and neck coil. In the illustration, a plastic bag has been used to line an interior of the outer shell, but the plastic bag is not required.
Figure 7D:
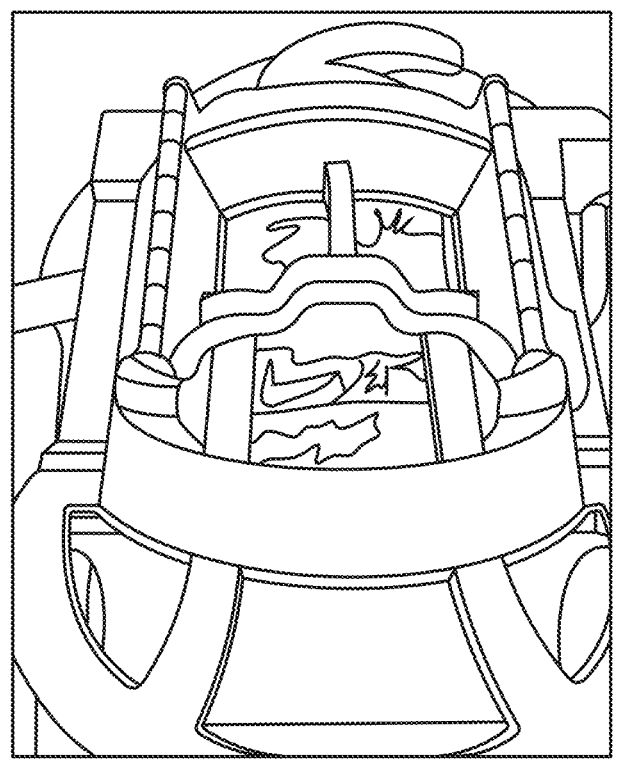
FIG. 7D also illustrates the outer shell of FIG. 7A placed within an MRI manufacturer's head and neck coil with the top coil elements secured in place over the outer holder. In the illustration, a plastic bag has been used to line an interior of the outer shell, but the plastic bag is not required.

Referring to FIGS. 6A-6C, the outer shell 300 is configured to receive one of the primary sample holder 100 and the secondary sample holder 200 for imaging. The outer shell 300 may contain the liquid in which the biological sample 400 is immersed in during imaging. In some examples, the walls of the outer shell 300 are thin (i.e., 1 mm or less, preferably, 0.5 mm) to bring the primary sample holder 100 or secondary sample holder 200 containing the biological sample 400 as close to the MM head coil as possible for improving imaging quality (similar concepts apply to other imaging modalities).

In other embodiments, the walls of this outer shell 300 may be hollow and filled with a material that potentially improves the MRI quality through increased permittivity (e.g., salt solution, ceramic or glass) and/or susceptibility matching to the biological sample 400. The material chosen for these properties will depend on the Mill field strength used. The solution or filling material may also be invisible to the imaging modality (e.g., deuterated water, which is also advantageous dues to its permittivity). In additional examples, the outer shell 300 may be formed from concentric first and second shells, where the first shell is closest to the biological sample 400 and the second shell forms the exterior of the outer shell 300. In these examples, the second shell may be made of a high permittivity, MM-invisible material.

In some embodiments, the outer shell 300 includes an additional outward component configured to stabilize and position the primary sample holder 100 or the secondary sample holder 200 ideally in the imaging device. The additional outward component may be manufactured to fit exactly within a specific commercially available imaging device (e.g., a 64-channel head and neck MRI coil for 3-T). Alternatively, the outer shell 300 may be sized and shaped to mimic common dimensions of the head and neck regions of a human so that it would be relatively universal in fitting into specific vendor products. In other examples, the outer shell 300 may also be configured to support or include a custom design for use in conjunction with an Mill coil to further improve signal to noise (e.g., a multiple channel coil that tightly apposes the boundaries of the primary sample holder 100 or the secondary sample holder 200).

FIGS. 6A and 6B depict an example of an outer shell that can also serve as a reservoir for the fluid in which the primary sample holder or the secondary sample holder is immersed when using Mill as the imaging modality for the radiology-pathology correlations. The outer shell is made from a material that is MM or CT compatible and can be made translucent or with fiducials for exact positioning of the primary sample holder 100 or the secondary sample holder and the biological sample therein. As depicted in FIGS. 6A and 6B, the volume of the outer shell 300 is large, but future versions may purposefully reduce this volume to reduce the field-of-view required for imaging. The walls of the outer shell 300 can be filled with material that matches the susceptibility of the biological sample 400 and/or that increases permittivity (to boost signal significantly) and/or that is MRI invisible.

As shown in FIGS. 7A-7D, the outer shell fits into an MRI coil. In the prototype, the dimensions of the outer shell were derived from a CT-image of a specific vendor coil (i.e., the 64-channel head & neck coil from Siemens Healthcare) (see FIG. 6C) so that the outer shell stabilizes the primary sample holder or the secondary sample holder and the biological sample therein. By fitting the shape of the coil (which was designed for the human head in a living subject), the outer shell is stable and ensures that the biological sample (e.g., the brain or hemisphere sample) is as close to individual MRI coil elements as possible (ensuring highest potential signal-to-noise). Similar design principles may apply to other imaging devices (e.g. CT or PET scanner). Similar design principles may also apply to a coil designed specifically for the type of biological sample (e.g., organ or tissue) being imaged.

Figure 15:
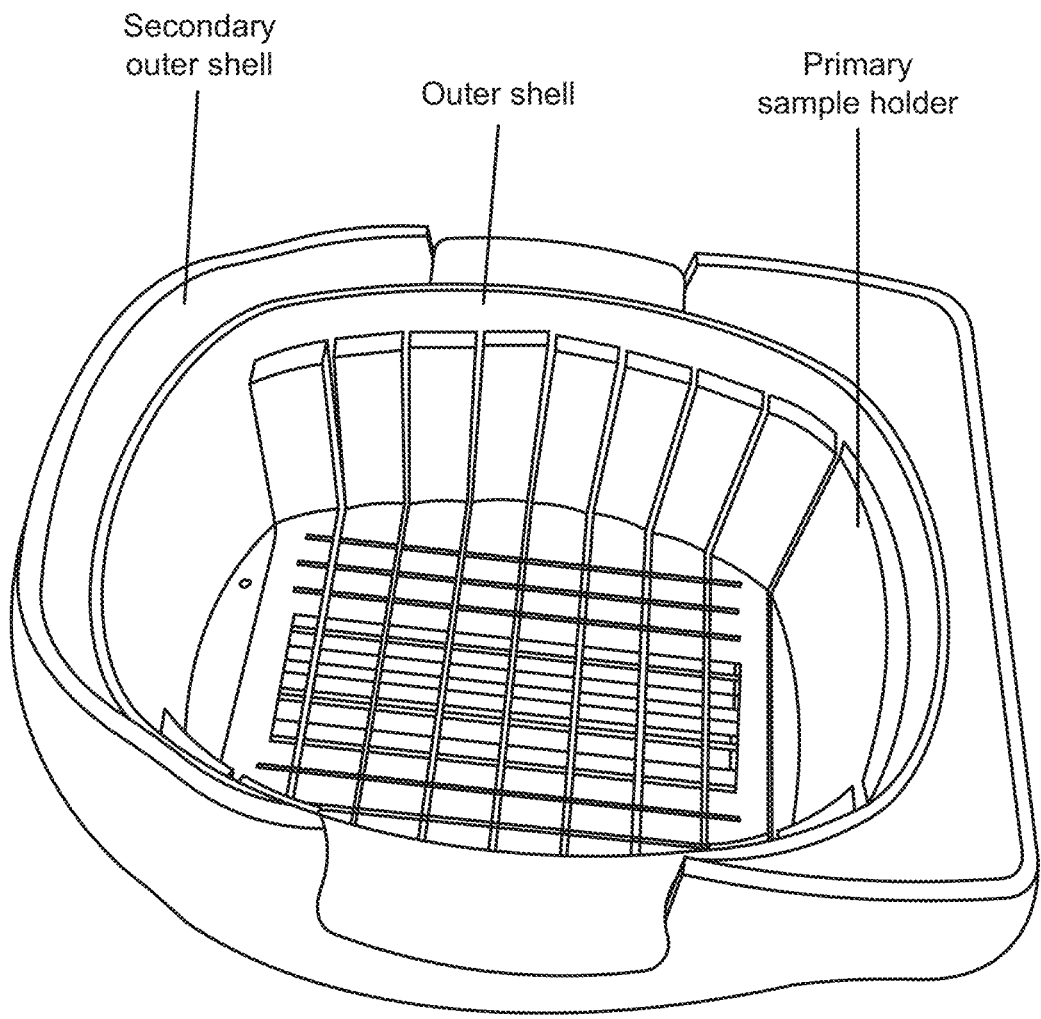
FIG. 15 illustrates a perspective photograph of a three-part system where the inner primary sample holder (similar to the primary sample holder of FIGS. 11A-11C) is combined with the outer shell (similar to the outer shell of FIGS. 12A-12D), and then placed in a secondary outer shell (similar to the outer shell of FIGS. 6A-6C) customized to fit perfectly within a specific manufacturer's MRI imaging coil. The space between the outer shell and the secondary outer shell may contain air and/or a susceptibility-matching fluid, material, or ceramic configured to improve the MRI signal-to-noise for the biological sample in the primary sample holder.

In some examples, a plurality of outer shells may be used. FIG. 15 illustrates a perspective photograph of a three-part system where the inner primary sample holder (similar to the primary sample holder of FIGS. 11A-11C) is placed within the outer shell (similar to the outer shell of FIGS. 12A-12D). The outer shell containing the primary sample holder is then placed in a secondary outer shell (similar to the outer shell of FIGS. 6A-6C) customized to fit within a specific manufacturer's MRI imaging coil. The space between the outer shell and the secondary outer shell may contain air and/or a susceptibility-matching fluid, material, or ceramic configured to improve the MRI signal-to-noise for the biological sample in the primary sample holder.

Figure 16A:
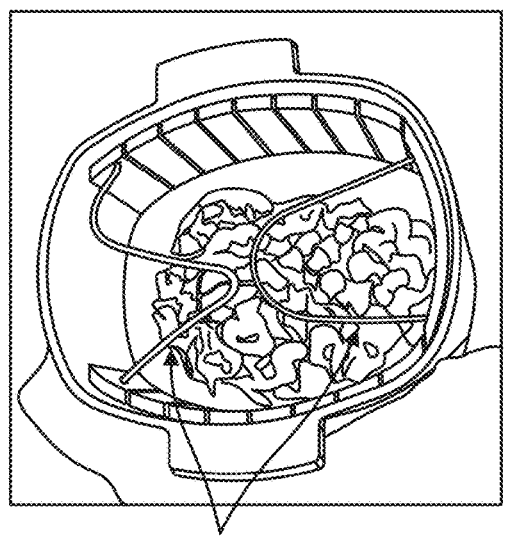
FIG. 16A illustrates a non-limiting example in which the biological sample is a brain hemisphere immersed in water inside of the primary sample holder of FIGS. 11A-11C and 15, which has been placed inside of the outer shell of FIGS. 12A-12D and 15.
Figure 16C:
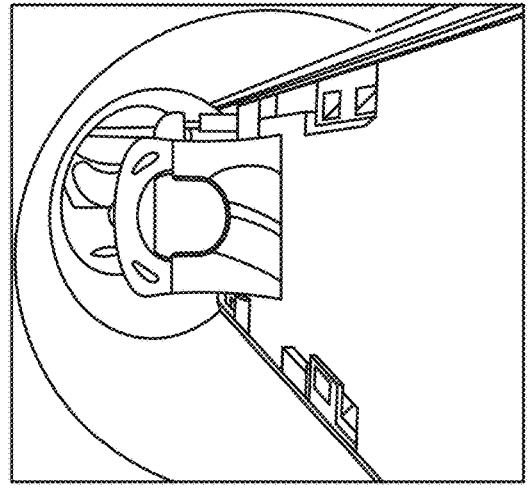
FIG. 16C illustrates the components of FIG. 16B inserted into a bore of a magnet for imaging.
Figure 16B:
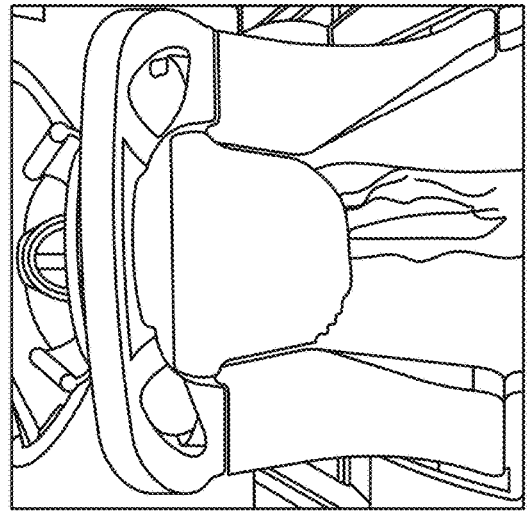
FIG. 16B illustrates the brain hemisphere, primary sample holder, and outer shell placed in a secondary outer shell sized to fit a specific MRI radiofrequency coil, in this example, a 64-channel Siemens head and neck coil.
Figures 16D, 16E, 16F:
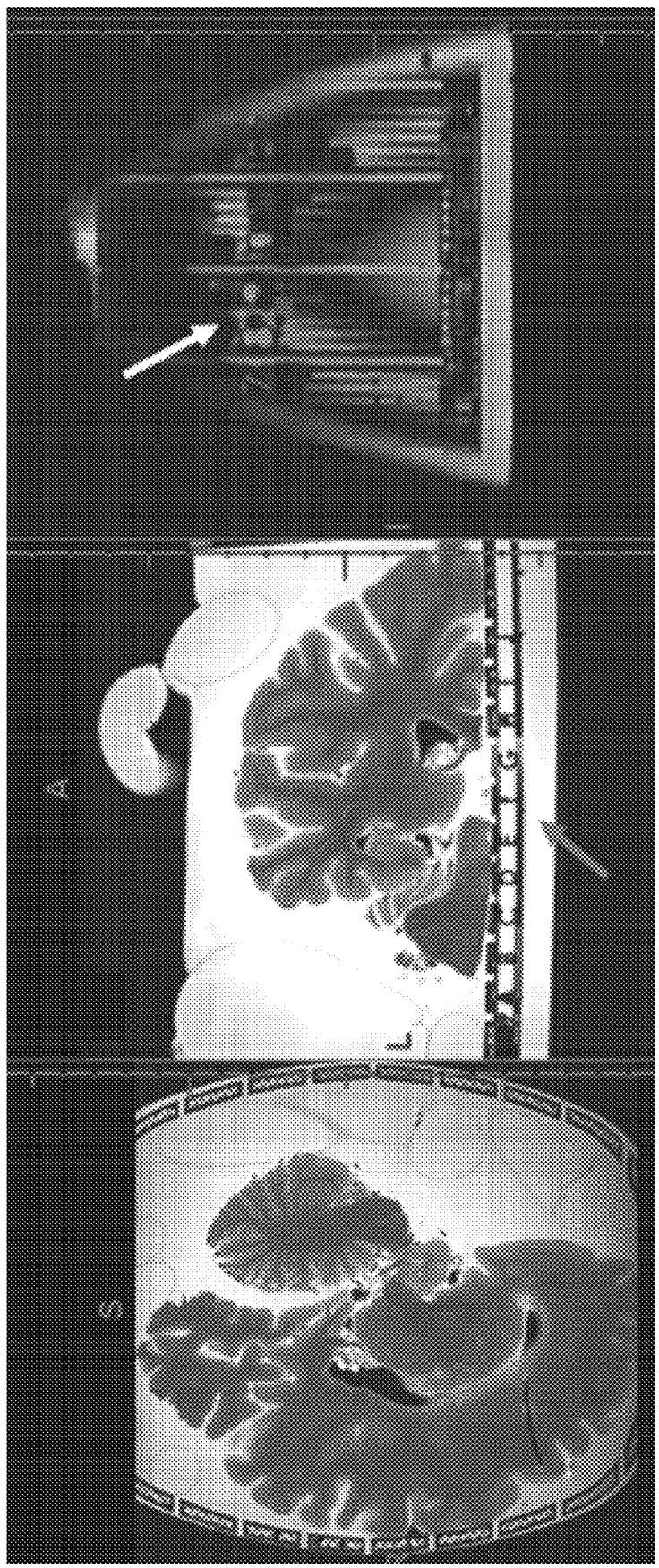
FIG. 16D is an image of the brain secured in the components of FIG. 16B obtained using MRI in the sagittal plane relative to the brain.
FIG. 16E is an image of the brain secured in the components of FIG. 16B obtained using MRI in the coronal plane relative to the brain.
FIG. 16F is an image of the walls of the device with the brain secured in the components of FIG. 16B obtained using MRI in the axial plane relative to the brain.

FIGS. 16A-16F demonstrate the use of the primary sample holder, outer shell, and secondary outer shell of FIGS. 11-13 and 15. FIG. 16A illustrates a non-limiting example in which the biological sample is a brain hemisphere immersed in water inside of the primary sample holder of FIGS. 11A-11C and 15, which has been placed inside of the outer shell of FIGS. 12A-12D and 15. FIG. 16B illustrates the brain hemisphere, primary sample holder, and outer shell placed in a secondary outer shell sized to fit a specific MM radiofrequency coil, in this example, a 64-channel Siemens head and neck coil with the overlying coil elements secured. FIG. 16C illustrates the brain hemisphere, primary sample holder, outer shell and secondary outer shell inserted into a bore of a magnet for imaging. FIGS. 16D-16F are images of the brain secured in the primary sample holder, outer shell and secondary outer shell, where the images were obtained using MRI in the sagittal, coronal, and axial plane, respectively, relative to the brain hemisphere. In FIG. 16E, the fiducials in the floor (small notches) are labeled with letters (see arrow). In FIG. 16F, numerical fiducials (see arrow) for the different cutting planes can be seen through the wall of the primary sample holder.

In any of the examples above, the fit between the primary sample holder or the secondary sample holder and the outer shell is relatively tight to prevent undesired motion, vibration or rotation of the primary sample holder (and sample) or the secondary sample holder (and sample) during imaging or transportation. In any of the examples above, the walls of the outer shell may be coated with epoxy or other material to further prevent leakage of liquid. In any of the examples above, the corners or other columns of the device are configured to hold securing attachments, including but not limited to string, flexible cords or rubber bands (see FIG. 16A) that will be used to hold the biological sample (e.g., brain, organ or organ part) firmly against the bottom of the primary sample holder so that the biological sample does not move during transportation into/out of the imaging device, between imaging and histology, or during the imaging or cutting process. The securing attachments can be overlapped or crossed for better securing the sample. The securing attachments are made of materials that will not interfere with imaging the biological sample in the magnet.

Method of Use

Use of the apparatus allow a user to obtain slices of regularly-spaced and uniform cuts (e.g., uniform thickness of the slices) of a biological sample such as the whole brain or hemisphere in the desired plane relative to any desired coordinate system (axial, coronal, sagittal or oblique). Use of the apparatus facilitates highly accurate stereotactic co-localization of gross pathology, histological and imaging findings for radiology-pathology correlations in clinical practice and research.

In a method of using the apparatus, the biological sample 400 is placed within the primary sample holder 100 and aligned with the anterior-posterior commissure plane using the grid 120 as guidance. Although the following description refers to the primary sample holder 100, one of ordinary skill in the art would understand that similar concepts apply to use of the primary sample holder 100A. The primary sample holder 100 is then placed within the outer shell 300. The outer shell 300 is then placed within an imaging coil (see FIG. 9A). The outer shell 300 may be filled with liquid to immerse the primary sample holder 100 and the biological sample 400 therein during imaging. Fluids could include, but are not limited to, water, phosphate buffer, formaldehyde or other fixative solution, or susceptibility matching fluid such as $D_2O$, fomblin or fluorinert. In some embodiments, a bag of the same or different fluid may be placed over the top of the biological sample 400 in the primary sample holder 100 to prevent sample motion during imaging and to improve the imaging characteristics of the biological sample 400 (e.g., $D_2O$ to improve signal in the biological sample itself).

Figures 8A, 8B:
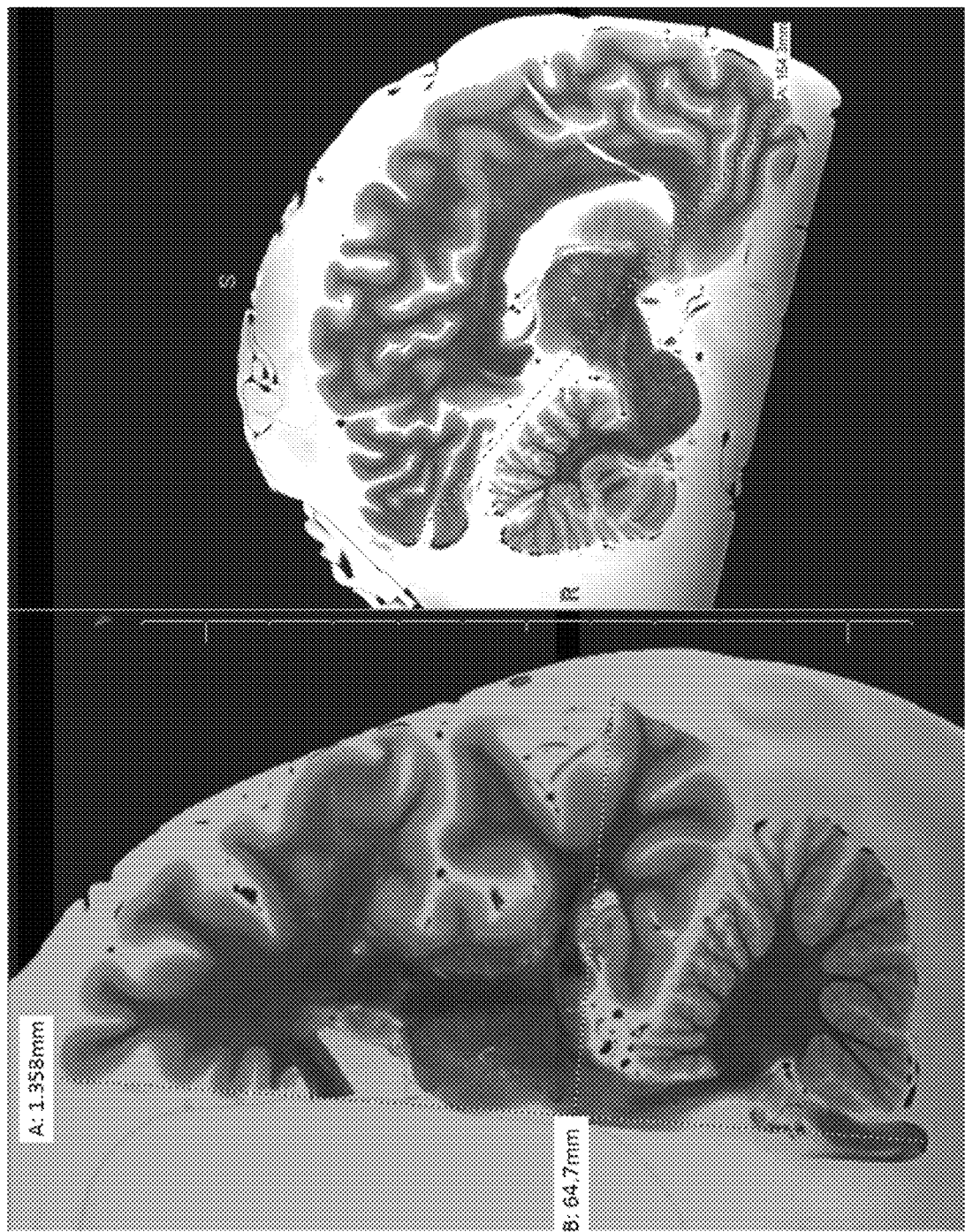
FIG. 8A illustrates a coronal image from T2-weighted MIll demonstrating typical dimensions of a cerebral hemisphere, which may be used as the biological sample.
FIG. 8B illustrates a sagittal image from T2-weighted MM demonstrating typical dimensions of a cerebral hemisphere, which may be used as the biological sample.
Figure 9B:
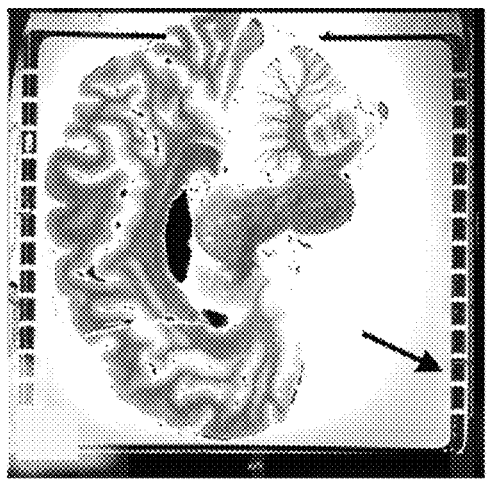
FIG. 9B illustrates a T2-weighted image transversely through the primary sample holder (and parasagittal through the brain hemisphere) where the slots for cutting the brain in the coronal plane after MM is completed are visible above and below the brain (see arrow).
Figure 9D:
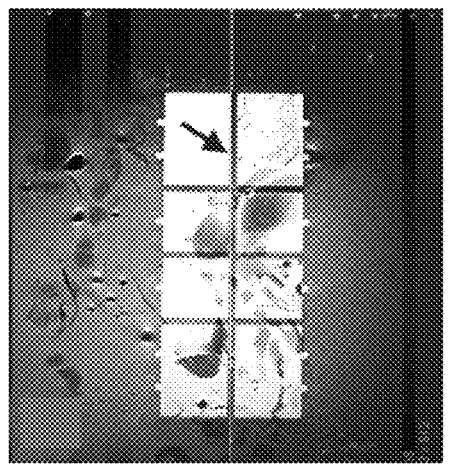
FIG. 9D is a T2-weighted image through the bottom wall or floor of the primary sample holder 100 showing alignment of the cerebral hemisphere anterior-posterior commissure line with the midline crossbar of the device (see arrow).
Figure 9A:
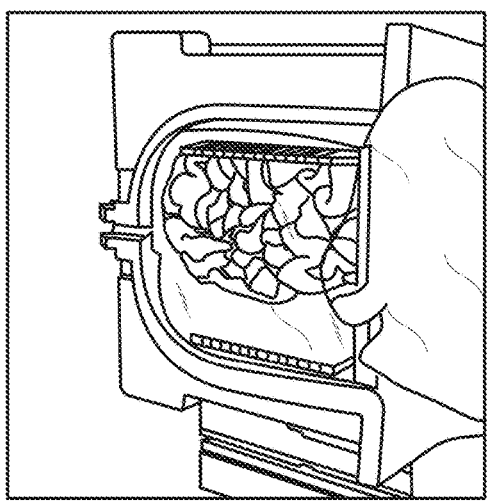
FIG. 9A illustrates the outer shell of FIG. 6A enclosing the primary sample holder of FIG. 1A holding a biological sample, where the outer shell is positioned in a 64-channel head and neck coil on a 3-T MIll scanner.
Figure 9C:
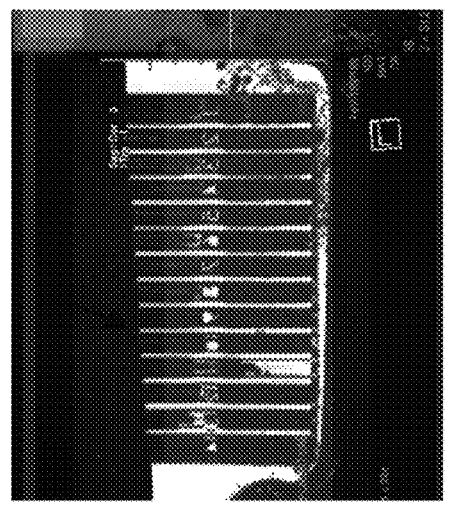
FIG. 9C illustrates a T2-weighted image through the side-wall of the primary sample holder 100 demonstrating the slots and the fiducial markers thereon (here backwards because of the orientation of the image).
Figures 10A, 10B, 10C:
FIG. 10A illustrates a coronal 1-mm CT slice of a cerebral hemisphere in the primary sample holder. The single bright spot in the device below the sample is the AC_PC orientation line shown in panel 9D (arrow), but here also detectable with CT contrast instead of MRI.
FIG. 10B illustrates an axial 1-mm CT slice of a cerebral hemisphere in the primary sample holder.
FIG. 10C illustrates a sagittal 2 mm slice of a cerebral hemisphere in the primary sample holder. The left side-wall of the primary sample holder 100 demonstrating the slots is visible in the image.

FIGS. 8A and 8B illustrate, respectively, coronal and sagittal images from T2-weighted MRI of a biological sample in a prototype of the sample holder that fits the contours of the MRI head coil. Here, the cerebral hemisphere measures 6.5×13.6×15.4-cm, LR×CC×AP dimensions. FIG. 9A illustrates a simple rectangular volume plastic container as a prototype outer shell 300 enclosing the primary sample holder 100 holding a biological sample 400 (i.e., a cerebral hemisphere) positioned in a 64-channel head and neck coil on a 3-T MRI scanner. FIG. 9B illustrates a T2-weighted image horizontal through the primary sample holder 100 (and sagittal through the brain hemisphere) where the slots 110 for cutting the brain in the coronal plane after MRI is completed are visible (see arrow). FIG. 9C illustrates a T2-weighted image through the side-wall of the primary sample holder 100 demonstrating the slots 110 and the fiducial markers thereon (here backwards because of the orientation of the image). FIGS. 9B and 9C are cross-references such that a user of the apparatus can precisely localize the imaging finding or structure for stereotaxis and correlative histology. FIG. 9D is a T2-weighted image through the bottom wall 104 of the primary sample holder 100 showing alignment of the cerebral hemisphere anterior-posterior commissure line with the midline crossbar of the device (see arrow). Because the side-walls maintain a consistent spatial relationship to this fiducial, this ensures that correlative brain cutting and histology are consistently oriented relative to the plane created by this brain internal reference. FIGS. 10A-10C illustrate coronal, axial, and sagittal, respectively, 2 mm slices of a cerebral hemisphere in the primary sample holder 100. The 2 mm slice reconstructions with minimum intensity projection demonstrate that the primary sample holder 100 will be compatible with multiple imaging modalities.

After imaging, the primary sample holder 100 is removed from the outer shell 300 and placed on a flat surface. Based on the images acquired (see, e.g., FIGS. 9B-9D), the biological sample 400 is cut into slices of predetermined thickness and orientation by inserting the cutting device 500 into the slots 110 of the primary sample holder 100. In order to acquire a smaller sample size, a slice obtained by cutting the biological sample 400 within the primary sample holder 100 may be placed in the secondary sample holder 200 for cutting in one or two additional planes. In particular, the slice is laid flat in the secondary sample holder 200 and aligned with one of the front wall 201, the back wall 202, or the side walls 203 so that the stereotactic coordinates in the primary sample holder 100 are reproduced in the secondary sample holder 200. The slice can then be cut in one additional plane by inserting the cutting device 500 into the slots 210 of the front wall 201 and the back wall 202, in a second additional plane by inserting the cutting device 500 into the slots 210 of the side walls 103, or a combination thereof. The samples obtained from cutting within the secondary sample holder 200 have precise stereotactic localization relative to the image obtained (FIGS. 9B-9D) when the biological sample 400 was imaged in the primary sample holder 100.

The samples obtained from cutting within the secondary sample holder 200 may be imaged by placing the secondary sample holder 200 within the outer shell 300. The outer shell 300 is then placed within an imaging coil (see FIG. 9A). The outer shell 300 may be filled with liquid to immerse the secondary sample holder 200 and the samples therein during imaging. The samples obtained from cutting within the secondary sample holder 200 may then be cut again to further reduce the size of the sample, or stored.

When the apparatus is in use, it is not necessary to use the primary sample holder 100, the secondary sample holder 200 and the outer shell 300 simultaneously. In other words, the apparatus may be used with different combinations of its components. For example, the primary sample holder 100 may be used alone or the secondary sample holder 200 may be used alone in both the medical imaging and pathological (cutting) processes. In another example, the primary sample holder 100 may be used in both a first medical imaging process and a first round of a pathological (cutting) process, while the secondary sample holder 200 may be used in a second pathological (cutting) process and/or second medical imaging process, subsequent to the first medical imaging and first pathological (cutting) processes. In yet another example, the primary sample holder 100 alone may be placed within the outer shell 300, or the secondary sample holder 200 alone may be placed within the outer shell 300 for the medical imaging process.

Figure 14:
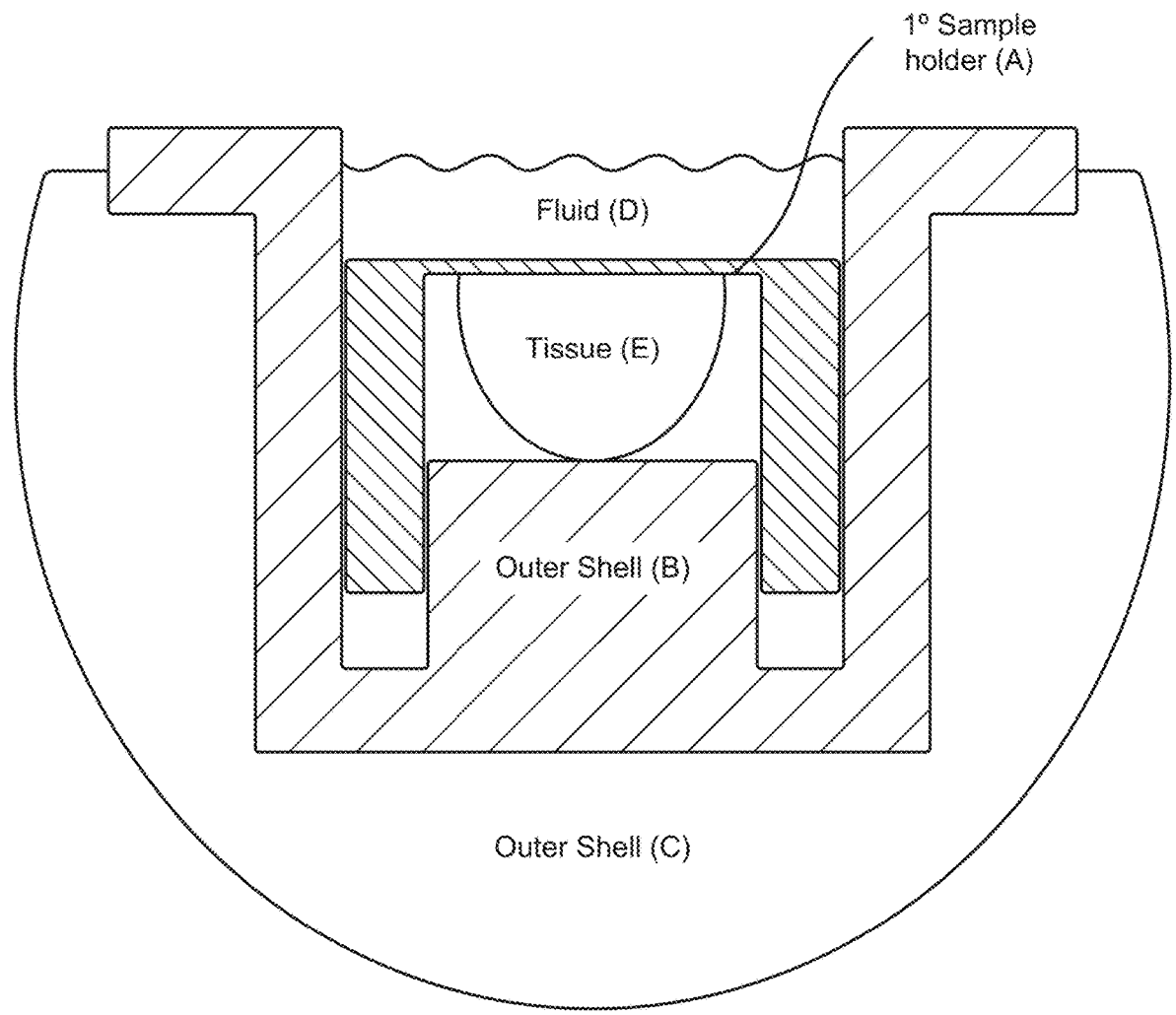
FIG. 14 illustrates a system for imaging, performing gross pathology, or determining histological correlations of a biological sample including a primary sample holder configured to receive the biological sample, and an outer shell configured to receive and hold the primary sample holder during an imaging process. The primary sample holder is inverted to secure the biological sample. The outer shell component labeled "B" may be used to contain liquid and fit the inner primary sample holder. This configuration inverts the biological sample, which may have advantages for the removal of air or gas from the biological sample, and allow more direct visualization of the alignment of the biological sample with the alignment fiducials in the bottom (or top as oriented) of the primary sample holder ("A"). In this position, the primary sample holder also lightly compresses the biological sample to restrict motion during the imaging.

FIG. 14 illustrates an alternative method of using the primary sample holder and the outer shell. As illustrated in FIG. 14, the outer shell includes a first component (B) and a second component (C) configured to receive the first component (B). The primary sample holder (A) is inverted to secure the biological sample (E). The bottom wall or floor of the primary sample holder (A) is on top such that a user can align the biological sample (E) to the floor fiducial markers (e.g., AC-PC line for a brain hemisphere). The walls of the primary sample holder (A) fit into/are configured to removably and reversibly slide within wells formed in the first component (B) of the outer shell that contains fluid (D), which may be used for imaging. The inversion of the primary sample holder (A) allows the dimensions where the sample is held to be adjusted so that the lower surface of the biological sample (E) contacts the internal floor of the first component (B) of the outer shell, thereby preventing sample movement. By inverting the primary sample holder (A), alignment to fiducials can be visually confirmed during placement, transportation, and imaging, and the biological sample (E) is better positioned for degassing of air if required. After imaging, the fluid (D), the primary sample holder (A) and the biological sample (E) may be removed from the first component (B) of the outer shell. The biological sample (E) may need to be re-aligned prior to cutting using the slots in the side walls as illustrated in other figures. The second component (C) of the outer shell is configured to fit the contours of an MRI coil and hold the first component (B) of the outer shell in place positioned closest to the MRI coil elements so that optimal signal is obtained.

The apparatus described in any of the embodiments above, allows for imaging, cutting multiple individual biological samples in a same manner, and/or stereotaxis without having to create custom templates for cutting individual biological samples.

The apparatus described in any of the embodiments above, provides a cutting template for routine gross pathology and simultaneously, an imaging template for CT, MIII or other modalities. These functions can be done independently to different levels of rigor, but the apparatus also provides a strong means to link the specific coordinates of the biological sample across these modalities. For example, in some aspects, the apparatus may be used solely for cutting a biological sample with stereotaxis, where no imaging is required or subsequently performed. In other aspects, the apparatus may be used solely for imaging a biological sample, where no cutting is required or subsequently performed (e.g., imaging a pre-cut sample or a whole sample). The apparatus and method described in any of the embodiments above may be used for postmortem biological samples or for biological samples obtained from living organisms, for example, during surgery.

One of ordinary skill in the art would appreciate that degassing a biological sample is an important problem when imaging ex vivo biological samples. The apparatus described in any of the embodiments above can be used to hold the biological sample in place when placed under a vacuum to remove air bubbles. For example, FIGS. 7A-7D illustrate an inverted primary sample holder such that the biological sample (e.g., brain hemisphere) is positioned to have its internal openings in a non-dependent position that should accelerate removal of air.

The construction and arrangements of the apparatus for stereotactic tissue sampling and radiology-pathology correlations, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, data processing algorithms, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

What is claimed:

1. A system for imaging, gross pathology, or histological correlations of a biological sample comprising:
a primary sample holder configured to receive the biological sample, the primary sample holder comprising:
an enclosure having a first side wall, a second side wall, and a bottom wall connected to the first side wall and the second side wall;
a plurality of slots provided at predetermined intervals along the first and second side walls, each of the slots extending from a top of a respective one of the first side wall or the second side wall to a bottom of the respective one of the first side wall or the second side wall; and
a grid recessed within the bottom wall, the grid comprising a hole bisected by a central panel that runs along a longitudinal axis of the primary sample holder and at least one axial panel that intersects the central panel along a length thereof,
wherein the plurality of slots are configured to receive a cutting device configured to cut the biological sample into slices containing a region of interest, and
wherein the biological sample received by the primary sample holder is configured to be aligned with the central panel of the grid to align the biological sample along an accepted internal orientation line for imaging, cutting multiple individual biological samples in a same manner, and/or stereotaxis.

2. The system of claim 1, wherein a top surface of the central panel and a top surface of the at least one axial panel is flush with a top surface of the bottom wall.

3. The system of claim 1, further comprising:
a secondary sample holder configured to receive at least one slice of the biological sample produced in the primary sample holder, the secondary sample holder comprising:
a second enclosure having a front wall, a back wall, a first side wall, a second side wall, and a bottom wall; and
a plurality of slots provided at predetermined intervals along the front wall, the back wall, the first side wall and the second side wall of the second enclosure, each of the slots extending from a top of a respective one of the front wall, the back wall, the first side wall and the second side wall of the second enclosure to a bottom of the respective one of the front wall, the back wall, the first side wall and the second side wall of the second enclosure,
wherein the plurality of slots provided in the front wall, the back wall, the first side wall and the second side wall of the second enclosure are configured to receive the cutting device to cut at least one slice of the biological sample produced in the primary sample holder in one or two additional planes.

4. The system of claim 3, wherein the secondary sample holder further comprises:
a plurality of linear indentations formed in the bottom wall of the second enclosure, the plurality of linear indentations forming a second grid configured to assist in reproduction of an orientation of the at least one slice produced in the primary sample holder.

5. The system of claim 1, further comprising an outer shell configured to receive and hold the primary sample holder during an imaging process.

6. The system of claim 3, further comprising an outer shell configured to receive and hold either the primary sample holder or the secondary sample holder during an imaging process.

7. The system of claim 5, wherein:
the primary sample holder further comprises a grid recessed within the bottom wall, the grid comprising a hole bisected by a central panel that runs along a longitudinal axis of the primary sample holder and at least one axial panel that intersects the central panel along a length thereof,
the outer shell comprises an inner component and an outer component,
the primary sample holder is configured to be inverted and received within at least one well formed in the inner component of the outer shell to secure the biological sample between the bottom wall of the primary sample holder and the inner component of the outer shell, and
the biological sample is configured to be aligned with the central panel of the grid to align the biological sample along an accepted internal orientation line for imaging.

8. The system of claim 7, wherein the primary sample holder and the biological sample therein are configured to be submerged in a fluid contained in the inner component of the outer shell during imaging.

9. The system of claim 5, further comprising a secondary outer shell configured to receive and hold the outer shell during the imaging process,
wherein a space between the secondary outer shell and the outer shell contains air and/or a susceptibility-matching fluid, material, or ceramic configured to improve a signal-to-noise ratio for the biological sample in the primary sample holder.

10. The system of claim 1, further comprising at least one securing attachment configured to hold the biological sample against the bottom wall of the primary sample holder such that the biological sample does not move during transportation into/out of an imaging device, between imaging and histology, or during an imaging or cutting process.

11. The system of claim 1, further comprising an imaging device configured to image the biological sample.

12. A system for imaging, gross pathology, or histological correlations of a biological sample comprising:
a primary sample holder configured to receive the biological sample, the primary sample holder comprising:
an enclosure having a first side wall, a second side wall, and a bottom wall connected to the first side wall and the second side wall; and
a plurality of slots provided at predetermined intervals along the first and second side walls, each of the slots extending from a top of a respective one of the first side wall or the second side wall to a bottom of the respective one of the first side wall or the second side wall; and
a secondary sample holder configured to receive at least one slice of the biological sample produced in the primary sample holder, the secondary sample holder comprising:
a second enclosure having a front wall, a back wall, a first side wall, a second side wall, and a bottom wall; and
a plurality of slots provided at predetermined intervals along the front wall, the back wall, the first side wall and the second side wall of the second enclosure, each of the slots extending from a top of a respective one of the front wall, the back wall, the first side wall and the second side wall of the second enclosure to a bottom of the respective one of the front wall, the back wall, the first side wall and the second side wall of the second enclosure, wherein the plurality of slots are configured to receive a cutting device configured to cut the biological sample into slices containing a region of interest, and wherein the plurality of slots provided in the front wall, the back wall, the first side wall and the second side wall of the second enclosure are configured to receive the cutting device to cut at least one slice of the biological sample produced in the primary sample holder in one or two additional planes.

13. A system for imaging, gross pathology, or histological correlations of a biological sample comprising:

a primary sample holder configured to receive the biological sample, the primary sample holder comprising:

an enclosure having a first side wall, a second side wall, and a bottom wall connected to the first side wall and the second side wall; and a plurality of slots provided at predetermined intervals along the first and second side walls, each of the slots extending from a top of a respective one of the first side wall or the second side wall to a bottom of the respective one of the first side wall or the second side wall; and an outer shell configured to receive and hold the primary sample holder during an imaging process, wherein the plurality of slots are configured to receive a cutting device configured to cut the biological sample into slices containing a region of interest.

14. A system for imaging, gross pathology, or histological correlations of a biological sample comprising:

a primary sample holder configured to receive the biological sample, the primary sample holder comprising:

an enclosure having a first side wall, a second side wall, and a bottom wall connected to the first side wall and the second side wall; and a plurality of slots provided at predetermined intervals along the first and second side walls, each of the slots extending from a top of a respective one of the first side wall or the second side wall to a bottom of the respective one of the first side wall or the second side wall; and at least one securing attachment configured to hold the biological sample against the bottom wall of the primary sample holder such that the biological sample does not move during transportation into/out of an imaging device, between imaging and histology, or during an imaging or cutting process, wherein the plurality of slots are configured to receive a cutting device configured to cut the biological sample into slices containing a region of interest.

* * * * *